US 8,252,727 B2

(12) United States Patent
Karrer et al.

(10) Patent No.: US 8,252,727 B2
(45) Date of Patent: Aug. 28, 2012

(54) ANTIBODY DIVERSITY GENERATION

(75) Inventors: Erik Karrer, Fremont, CA (US); Steven H. Bass, Hillsborough, CA (US); Robert Whalen, Foster City, CA (US); Philip A. Patten, Portola Valley, CA (US)

(73) Assignee: Maxygen, Inc., San Mateo, CA (US)

( * ) Notice: Subject to any disclaimer, the term of this patent is extended or adjusted under 35 U.S.C. 154(b) by 176 days.

(21) Appl. No.: 12/026,412

(22) Filed: Feb. 5, 2008

(65) Prior Publication Data

US 2008/0207459 A1 Aug. 28, 2008

Related U.S. Application Data

(63) Continuation of application No. 10/686,945, filed on Oct. 16, 2003, now abandoned, which is a continuation of application No. 09/704,469, filed on Nov. 1, 2000, now abandoned.

(60) Provisional application No. 60/163,370, filed on Nov. 3, 1999, provisional application No. 60/176,002, filed on Jan. 12, 2000.

(51) Int. Cl.
*C07K 1/00* (2006.01)
*C12N 15/00* (2006.01)
*C40B 30/00* (2006.01)
*C40B 30/02* (2006.01)
*C40B 30/04* (2006.01)
*C40B 40/08* (2006.01)
*C40B 50/00* (2006.01)

(52) U.S. Cl. ............... 506/1; 506/17; 506/23; 506/7; 506/9; 424/133.1

(58) Field of Classification Search ............. 424/133.1; 506/1, 7, 9, 17, 23
See application file for complete search history.

(56) References Cited

U.S. PATENT DOCUMENTS

| 4,634,664 | A | 1/1987 | Oestberg |
| 4,634,666 | A | 1/1987 | Engleman et al. |
| 5,756,316 | A | 5/1998 | Schellenberger |
| 5,783,431 | A | 7/1998 | Peterson et al. |
| 5,824,485 | A | 10/1998 | Thompson et al. |
| 6,277,375 | B1 | 8/2001 | Ward ...................... 424/133.1 |

FOREIGN PATENT DOCUMENTS

| WO | WO 95/22625 A1 | 8/1995 |
| WO | WO 96/33207 A1 | 10/1996 |
| WO | WO 97/35957 A1 | 10/1997 |
| WO | WO 98/42727 A1 | 10/1998 |
| WO | WO 00/00632 A1 | 1/2000 |
| WO | WO 00/09676 A1 | 2/2000 |
| WO | WO 00/42559 A1 | 7/2000 |
| WO | WO 00/42560 A2 | 7/2000 |
| WO | WO 00/42560 A3 | 7/2000 |
| WO | WO 00/42561 A2 | 7/2000 |
| WO | WO 00/42561 A3 | 7/2000 |
| WO | WO 00/46344 A2 | 8/2000 |
| WO | WO 00/46344 A3 | 8/2000 |

OTHER PUBLICATIONS

Salfeld (Nature Biotech. 25(12): 1369-1372 (2007)).*
Dall'Acqua (J. Immunol. 177:1129-1138 (2006)).*
Zuckier et al. (Can Res. 58:3905-3908 (1998)).*
U.S. Appl. No. 09/407,800, filed Sep. 28, 1999, Maxygen, Inc.
U.S. Appl. No. 09/408,392, filed Sep. 28, 1999, Maxygen, Inc.
U.S. Appl. No. 09/408,393, filed Sep. 28, 1999, Maxygen, Inc.
U.S. Appl. No. 09/618,579, filed Jul. 18, 2000, Maxygen, Inc.
U.S. Appl. No. 60/186,482, filed Mar. 2, 2000, Maxygen, Inc.
Balint and Larrick (1993) "Antibody Engineering by Parsimonious Mutagenesis." *Gene* 137:109-118.
Chothia and Lesk (1987) "Canonical Structures for the Hypervariable Regions of Immunoglobulins." *J Mol Biol.* 196:901-917.
Giver et al. (1998) "Combinatorial protein design by in vitro recombination." *Current Opinion in Chemical Biology* 2(3): 335-338.
Gram et al. (1992) "In Vitro selection and affinity maturation of antibodies from a naïve combinatorial immunoglobulin library." *PNAS* 89:3576-3580.
Hawkins et al. (1992) "Selection of phage antibodies by binding affinity. Mimicking affinity maturation." *J. Mol Biol.* 226:889-896.
Hock (1997) "Antibodies for immunosensors: a review." *Analytica Chimica Acta* 347:177-186.
Huse et al. (1989) "Generation of a Large Combinational Library of the Immunoglobulin Repertoire in Phage Lambda." *Science* 246:1275-1281.
Jirholt et al. (1998) "Exploiting sequence space: shuffling in vivo formed complementarily determining regions into a master framework." *Gene* 215:471-476.
Litman et al. (1993) "Phylogenetic diversification on immunoglobulin genes and the antibody repertoire." *Mol Biol Evol* 10:60-72.
Low et al. (1996) "Mimicking somatic hypermutation: affinity maturation of antibodies displayed on bacteriophage using a bacterial mutator strain." *J. Mol Biol.* 260:359-368.
Marks et al. (1991) "By-passing immunization. Human antibodies from V-gene libraries displayed on phage." *J. Mol Biol.* 222:581-597.
Marks et al. (1992) "By-Passing Immunization: Building High Affinity Human Antibodies by Chain Shuffling." *Biotechniques* 10:779-782.
Schier and Marks (1996) "Efficient in vitro affinity maturation of phage antibodies using BIAcore guided selections." *Hum Antibodies Hybridomas* 7:95-105.
Stemmer et al. (1993) "Selection of an Active Single Chain Fv Antibody From a Protein Linker Library Prepared by Enzymatic Inverse PCR." *Biotechniques* 14(2):256-265.

(Continued)

*Primary Examiner* — Lynn Bristol
(74) *Attorney, Agent, or Firm* — Weaver Austin Villeneuve and Sampson LLP; Sharon Fujita

(57) ABSTRACT

Methods for improving antibodies by a variety of DNA diversification and selection procedures are provided. Improvements include increases in affinity, alterations in specificity and effector function, as well as reduced antigenicity, e.g. humanization. Libraries of recombinant antibody sequences are provided, as are cells expressing members of such libraries. Novel phage display vectors are provided. Methods for the coevolution of an antibody and its cognate antigen are provided. Coevolution is used to evolve HIV envelope proteins with increased antigenicity and broadly neutralizing antibodies that interact therewith. Methods of improving antibodies for use in the detection of biological warfare agents are provided.

12 Claims, No Drawings

OTHER PUBLICATIONS

Stemmer et al. (1995) "Single-step assembly of a gene and entire plasmid form large numbers of oligodeoxy-ribonucleotides." *Gene* 164:49-53.

Stemmer et al. (1997) "Molecular evolution of genes and pathways by DNA shuffling." *FASEB J.* 11:A1124.

Ward et al. (1989) "Binding activities of a repertoire of single immunoglobulin variable domains secreted from *Escherichia coli.*" *Nature* 341:544-546.

Winter et al. (1994) "Making Antibodies by Phage Display Technology." *Annu Rev. Immunol* 12:433-455.

Wu et al. (1970) "An analysis of the sequences of the variable regions of bence jones proteins and myeloma light chains and their implications for anti-body complementarity." *J. Exo Med.* 132:211-250.

Daugherty et al NAR 19:2471, 1991.

Rader et al PNAS 95:8910-15, 1998.

Rudikoff et al PNAS 79:1979, 1982.

Braunagel, M. and Little, M., "Construction of a semisynthetic antibody library using trinucleotide oligos", *Nucl Acids Res* (1997) 25(22):4690-4691.

Chargelegue, et al., "A Peptide Mimic of a Protective Epitope of Respiratory Syncytial Virus Selected from a Combinatorial Library Induces Virus-Neutralizing Antibodies and Reduces Viral Load In Vivo", *J Virol* (1998) 72(3):2040-2046.

Chen, et al., "Identification of multiple cancer/testis antigens by allogeneic antibody screening of a melanoma cell line library", *Proc. Natl. Acad. Sci. USA* (1998) 95:6919-6923.

Desai, et al., "Characterization of Human Anti-High Molecular Weight-Melanoma-associated Antigen Single-Chain Fv Fragments Isolated from a Phage Display Antibody Library", *Cancer Res* (1998) 58:2417-2425.

Fignini, et al., "Panning Phage Antibody Libraries on Cells: Isolation of Human Fab Fragments against Ovarian Carcinoma Using Guided Selection", *Cancer Res* (1998) 58:991-996.

Hirose, et al., "Isolation of anti-glutathione antibodies from a phage display library", *Protein Engineering* (1998) 11(3): 243-248.

Meurer, et al., "The effects of IB4, a monoclonal antibody to the CD18 Leukocyte integrin on phorbol myristate acetate (PMA)-iinduced polymorphonuclear leukocyte (PMN) accumulation and endothelial injury in rabbit lungs", *Inflammation*. (1999) 23(1):51-62 Abstract only.

Sheets, et al., "Efficient construction of a large nonimmune phage antibody library: The production of a high-affinity human single-chain antibodies to protein antigens", *Proc. Natl. Acad. Sci. USA* (1998) 95:6157-6162.

Smith, et al., Human Rhinovirous Type 14:Human Immunodeficiency Virus Type 1 (HIV-1) V3 Loop Chimeras from a Combinatorial Library Induce Potent Neutralizing Antibody Responses against HIV-1, *J Virol* (1998) 72(1):651-559.

Yano, et al., "Directed evolution of an aspartate aminotransferase with new substrate specificities" *Proc. Natl Acad. Sci. USA* (1998) 95:5511-5515.

Zhang, et al. "Directed evolution of a fucosidase from a galactosidase by DNA shuffling and screening" *Proc. Natl. Acad. Sci. USA* (1997) 94:4504-4509.

Zhu, et al., "Inhibition of Vascular Endothelial Growth Factor-induced Receptor Activation with Anti-Kinase Insert Domain-containing Receptor Single-Chain Antibodies from a Phage Display Library", *Cancer Res* (1998) 58:3209-3214.

\* cited by examiner

```
                         SEQUENCE LISTING

<160> NUMBER OF SEQ ID NOS: 6

<210> SEQ ID NO 1
<211> LENGTH: 100
<212> TYPE: PRT
<213> ORGANISM: Mus musculus

<400> SEQUENCE: 1

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
                20                  25                  30

Trp Asn Met Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
        50                  55                  60
```

Ser Val Lys Gly Arg Phe Thr Ile Ser Arg Asp Asp Ser Lys Ser Ala
65                  70                  75                  80

Val Tyr Leu Gln Met Ile Asp Leu Arg Ile Glu Asp Thr Gly Val Tyr
                85                  90                  95

Tyr Cys Ser Arg
            100

<210> SEQ ID NO 2
<211> LENGTH: 100
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Asn His Trp Val Arg Gln Ala Pro Gly Gln Gly Leu Glu Trp Met
            35                  40                  45

Gly Trp Ile Asn Pro Lys Ser Asn Ser Gly Asn Thr Lys Tyr Ser Gln
        50                  55                  60

Lys Phe Gln Gly Arg Val Thr Ile Thr Arg Asp Thr Ser Ala Ser Thr
65                  70                  75                  80

Ala Tyr Met Glu Leu Ser Ser Leu Arg Ser Glu Asp Thr Ala Val Tyr
                85                  90                  95

Tyr Cys Ala Arg
            100

<210> SEQ ID NO 3
<211> LENGTH: 100
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Asn His Trp Val Arg Gln Ala Pro Gly Gln Gly Leu Glu Trp Met
            35                  40                  45

Gly Trp Ile Asn Pro Lys Ser Asn Ser Gly Gly Thr Asn Tyr Ala Gln
        50                  55                  60

Lys Phe Gln Gly Arg Val Thr Ile Thr Arg Asp Thr Ser Ala Ser Thr
65                  70                  75                  80

Ala Tyr Met Glu Leu Ser Ser Leu Arg Ser Glu Asp Thr Ala Val Tyr
                85                  90                  95

Tyr Cys Ala Arg
            100

<210> SEQ ID NO 4
<211> LENGTH: 100
<212> TYPE: PRT
<213> ORGANISM: Homo sapiens

<400> SEQUENCE: 4

Gln Val Gln Leu Val Gln Ser Gly Ser Glu Leu Lys Lys Pro Gly Ala
1               5                   10                  15

Ser Val Lys Val Ser Arg Lys Ala Ser Gly Tyr Thr Phe Thr Gly Tyr

```
                        20                  25                  30

Tyr Asn Asn Trp Val Arg Gln Ala Pro Gly Gln Gly Leu Glu Trp Met
                35                  40                  45

Gly Trp Ile Asn Thr Lys Ser Asn Thr Gly Asn Pro Thr Tyr Ala Gln
        50                  55                  60

Gly Phe Thr Gly Arg Phe Val Phe Ser Leu Asp Thr Ser Val Ser Thr
 65                 70                  75                  80

Ala Tyr Leu Gln Ile Ser Ser Leu Lys Ala Glu Asp Thr Ala Val Tyr
                    85                  90                  95

Tyr Cys Ala Arg
            100

<210> SEQ ID NO 5
<211> LENGTH: 100
<212> TYPE: PRT
<213> ORGANISM: Homo sapiens

<400> SEQUENCE: 5

Gln Val Lys Leu Val Gln Ser Gly Ala Glu Val Lys Lys Pro Gly Val
 1               5                  10                  15

Ser Val Lys Val Ser Cys Lys Ala Ser Gly Ser Thr Val Thr Asn Tyr
                20                  25                  30

Ala Ile His Trp Val Arg Gln Ala Pro Gly Gln Arg Leu Glu Trp Met
                35                  40                  45

Gly Trp Ile Asn Ala Lys Ser Gly Asn Gly Asn Thr Lys Tyr Ser Gln
        50                  55                  60

Lys Phe Gln Gly Arg Val Thr Ile Thr Arg Asp Thr Ser Ala Asn Thr
 65                 70                  75                  80

Ala Tyr Met Glu Leu Ser Ser Leu Arg Ser Asp Thr Ala Val Tyr
                    85                  90                  95

Tyr Cys Ala Arg
            100

<210> SEQ ID NO 6
<211> LENGTH: 100
<212> TYPE: PRT
<213> ORGANISM: Homo sapiens

<400> SEQUENCE: 6

Gln Val Gln Leu Gln Glu Ser Gly Ala Glu Val Arg Lys Pro Gly Ala
 1               5                  10                  15

Ser Val Lys Val Ser Cys Lys Ala Ser Gly Tyr Ile Leu Thr Thr Tyr
                20                  25                  30

Tyr Asn His Trp Val Arg Gln Ala Pro Gly Gln Gly Leu Glu Trp Met
                35                  40                  45

Gly Leu Ile Asn Pro Lys Ser Ser Gly Gly Ser Gly Asn Ile His
        50                  55                  60

Lys Phe Gln Gly Arg Leu Thr Met Thr Arg Asp Thr Ser Thr Ser Thr
 65                 70                  75                  80

Val Tyr Met Glu Met Ser Ser Leu Arg Ser Glu Asp Thr Ala Val Tyr
                    85                  90                  95

Phe Cys Ala Arg
            100
```

ANTIBODY DIVERSITY GENERATION

CROSS REFERENCE TO RELATED APPLICATIONS

This application is a Continuation of U.S. application Ser. No. 10/686,945 filed Oct. 16, 2003 (now abandoned), which is a Continuation of U.S. application Ser. No. 09/704,469 filed Nov. 1, 2000 (now abandoned), which claims priority to and benefit of U.S. provisional application No. 60/163,370, filed Nov. 3, 1999, and U.S. provisional application No. 60/176,002, filed Jan. 12, 2000, the specifications of which are incorporated herein by reference in their entirety.

COPYRIGHT NOTIFICATION PURSUANT TO 37 C.F.R. §1.71(e)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to altered antibodies and antigen-binding fragments, methods for the production of altered antibodies and antigen-binding fragments, and therapeutic and other uses thereof. The present invention also relates to altered antibodies and antigen-binding fragments having improved antigen binding affinity and/or antigen binding specificity, methods for the production of such antibodies, and uses thereof.

BACKGROUND OF THE INVENTION

Antibodies are extremely valuable, both as therapeutic agents and as general reagents in a variety of molecular biological processes. Methods of producing polyclonal and monoclonal antibodies are available, as are many antibodies. A number of basic texts describe standard antibody production processes, including, e.g., Borrebaeck (ed) (1995) *Antibody Engineering, 2nd Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols Humana Press*, Towata, N.J. (Paul); Paul (ed.), (1993) *Fundamental Immunology*, Raven Press, N.Y.; Coligan (1991) *Current Protocols in Immunology Wiley/Greene*, N.Y.; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

Naturally occurring antibodies, or immunoglobulins (Igs), comprise a basic four polypeptide chain structure comprising two identical heavy (H) chains and two identical light (L) chains which are stabilized and cross-linked by intrachain and interchain disulphide bonds. Different antibody classes comprise variants of this four-chain structure. Each heavy chain comprises a variable domain at N-terminal followed by several constant domains. Each light chain has a variable domain at its N-terminal and one constant domain at its C-terminal. Because the largest amount of sequence variation is concentrated in the N-terminal domains of the light and heavy chains, each of these domains is termed a variable (V) domain (or "V region"). The constant domains make up the constant region, which comprises the remainder of the molecule and exhibits relatively little sequence variation. Heavy chains are comprised of five major types, depending on the antibody class, and consist of about 450-600 amino acid residues. Light chains are of two major types and have about 230 amino acid residues. Both heavy and light chains are folded into domains, comprising globular polypeptide regions.

In the antibody, the variable domain of the light chain is aligned with the variable domain of the heavy chain; the constant domain of the light chain is aligned with the first constant domain of heavy chain. The variable domains of each pair of light and heavy chains form the antigen binding site for binding the antibody to an epitope of the antigen. The constant domains in the light and heavy chains are not directly involved in antigen binding. Each heavy or light chain variable domain comprises four relatively conserved framework (FR) regions (or framework segments) which are separated and connected by three hypervariable or complementarity determining regions (CDRs), which are believed to contact the target antigen of the antibody and to be principally responsible for binding of the antibody to the antigen.

The framework regions and CDRs have been precisely defined. See, e.g., Kabat, E. A. et al., SEQUENCES OF PROTEINS OF IMMUNOLOGICAL INTEREST, US Dept. Health and Human Services, National Institutes of Health, USA ($5^{th}$ ed. 1991); and Wu et al., *J. Exo. Med.* 132:211-250 (1970), each of which is incorporated herein by reference in its entirety for all purposes. For additional discussion of the structure of variable domains, see Poljak, R. J. et al., *PNAS USA,* 70, 3305-3310, 1973; Segal, D. M. et al., *PNAS USA,* 71, 4298-4302, 1974; and Marquart, M. et al., *J. Mol. Biol.,* 141, 369-391, 1980, each of which is incorporated herein by reference in its entirety for all purposes. The sequences of the framework regions of different light or heavy chains are relatively conserved within a species. The combined heavy and light chain framework regions of an antibody serve to position and align the CDRs for proper binding to the antigen.

The amino acids of the CDRs of the variable domains were initially defined by Kabat, based on sequence variability, to consist of amino acid residues 31-35 (H1), 50-65 (H2), and 95-102 (H3) in the human heavy chain variable domain ($V_H$) and amino acid residues 24-34 (L1), 50-56 (L2), and 89-97 (L3) in the human light chain variable domain ($V_L$), using Kabat's numbering system for amino acid residues of an antibody. See Kabat et al., SEQUENCES OF PROTEINS OF IMMUNOLOGICAL INTEREST, US Dept. Health and Human Services, NIH, USA (5th ed. 1991). Chothia and Lesk, *J. Mol. Biol.* 196:901-917 (1987) presented another definition of the CDRs based on residues that included in the three-dimensional structural loops of the variable domain regions, which were found to be important in antigen binding activity. Chothia et al. defined the CDRs as consisting of amino acid residues 26-32 (H1), 53-55 (H2), and 96-101 (H3) in the human heavy chain variable domain ($V_H$), and amino acid residues 26-32 (L1), 50-52 (L2), and 91-96 (L3) in the human light chain variable domain ($V_L$). Combining the CDR definitions of Kabat and Chothia, the CDRs consist of amino acid residues 26-35 (H1), 50-65 (H2), and 95-102 (H3) in human $V_H$ and amino acid residues 24-34 (L1), 50-56 (L2), and 89-97 (L3) in human $V_L$, based on Kabat's numbering system.

V genes encode the approximately N-terminal 95 amino acids of the V domains. The number of V genes at each locus varies between loci and species, but may include up to about several hundred V genes.

Antibody heavy chain V domains include V genes, D (diversity) genes, and J (joining) genes. The large diversity in antibody variable domains results from, in part, recombination between V, D, and J gene segments. To produce a gene encoding a heavy chain variable domain, any one of the heavy chain variable domain genes is recombined with any one of a small number of D and J genes to produce a VDJ gene. The recombination process of a light chain variable domain is similar, except that a V gene is recombined directly with a J gene, since light chain variable domains have no D gene segments.

Over the last decade, a variety of recombinant techniques for antibody preparation which do not rely on injection of an antigen into an animal have been developed. For example, it is possible to generate and select libraries of recombinant antibodies in phage or similar vectors. See, e.g., Winter et al. (1994) "Making Antibodies by Phage Display Technology" *Annu. Rev. Immunol.* 12:433-55 and the references cited therein for a review. See also, Griffiths and Duncan (1998) "Strategies for selection of antibodies by phage display" *Curr Opin Biotechnol* 9: 102-8; Hoogenboom et al. (1998) "Antibody phage display technology and its applications" *Immunotechnology* 4: 1-20; Gram et al. (1992) "in vitro selection and affinity maturation of antibodies from a naïve combinatorial immunoglobulin library" *PNAS* 89:3576-3580; Huse et al. (1989) *Science* 246: 1275-1281; and Ward, et al. (1989) *Nature* 341: 544-546. Kits for cloning and expression of recombinant antibody phage systems are known and available, e.g., the "recombinant phage antibody system, mouse ScFv module," from Amersham-Pharmacia Biotechnology (Uppsala, Sweden). Bacteriophage antibody libraries have also been produced for making high affinity human antibodies by chain shuffling (Marks et al. (1992) "By-Passing Immunization: Building High Affinity Human Antibodies by Chain Shuffling" *Biotechniques* 10:779-782.

In general, the libraries include repertoires of V genes (e.g., harvested from populations of lymphocytes or assembled in vitro) which are cloned for display of associated heavy and light chain variable domains on the surface of filamentous bacteriophage. Phage are selected by binding to an antigen. Soluble antibodies are expressed from phage infected bacteria and the antibody can be improved, e.g., via mutagenesis. For example, Stemmer et al. (1993) "Selection of an Active Single Chain Fv Antibody From a Protein Linker Library Prepared by Enzymatic Inverse PCR" *Biotechniques* 14(2): 256-65 describes production of large libraries of site directed single chain Fv antibody mutants. Other references also propose library mutagenesis strategies, such as computer assisted oligo directed scanning mutagenesis. See, e.g., Balint and Larrick (1993) "Antibody Engineering by Parsimonious Mutagenesis" *Gene* 137:109-118.

More recently, forced evolution methods have been adapted to recombinant antibody construction and improvement methods to produce optimized antibodies. For example, Crameri et al. (1996) "Construction and evolution of antibody-phage libraries by DNA shuffling" *Nature Medicine* 2:100-103 describe, e.g., the construction and evolution of antibody-phage libraries by a variety of DNA recombination procedures, e.g., DNA shuffling. Crameri and Stemmer (1995) "Combinatorial multiple cassette mutagenesis creates all the permutations of mutant and wildtype cassettes" *BioTechniques* 18:194-195 describe, e.g., in vitro recombination of antibody DNA fragments (scFv fragments) by combinatorial multiple cassette mutagenesis.

A variety of patents by the inventors and their co-workers provide additional details on diversification procedures, e.g., shuffling, applicable to the directed evolution of antibodies, including U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;" U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "METHODS AND COMPOSITIONS FOR CELLULAR AND METABOLIC ENGINEERING."

For example, the '793 patent details improvement of antibodies involving diversification, e.g., by DNA shuffling, of a library of mutant CDRs. The '721 patent details, e.g., peptide display methods and antibody display and screening methods. In general, a variety of antibody diversification are found throughout the noted patents.

Although methods of producing antibodies by making, screening and evolving antibodies and antibody libraries are established, it would be desirable to have additional techniques for antibody generation and refinement. Furthermore, a general technology platform for addressing these issues would be desirable. The present invention provides these and other features which will be apparent upon a complete review of the following.

SUMMARY OF THE INVENTION

The present invention relates to a new technology platform for producing antibodies involving the diversification of antibody encoding sequences, e.g., using a variety of recombination and mutagenesis procedueres including DNA shuffling methods. In addition, the invention provides for antigen-antibody co-evolution and for the improvement of a variety of antibodies of interest. Several methods of humanizing antibodies are also provided. Libraries of nucleic acids produced by the methods, as well as corresponding character strings in computer systems (e.g., sequence data corresponding to the nucleic acids of the library) are also provided. Cells comprising the library members and antibodies produced by the methods are provided.

As noted, the invention provides methods of modifying an initial antibody. For example, the initial antibody can be a known antibody such as one of those noted herein. In the methods, a first nucleic acid (or, for in silico aspects, a character string) encoding an initial antibody of Tables 1 and 2 (or a homologue or a fragment thereof) is diversified in one or more rounds of recombination, with or without additional mutagenic procedures, and screening/selection with one or more second character string or second antibody coding nucleic acid or second homologue or second fragment thereof. This produces a library of nucleic acids encoding modified antibodies and/or a data set of nucleic acid character strings encoding modified antibodies.

For example, the diversification can include recursively recombining the first nucleic acid or character string encoding an initial antibody of Table 1 or 2, or a homologue or fragment thereof, with one or more second character string or second antibody coding nucleic acid or second homologue or second fragment thereof to produce a library of nucleic acids encoding modified antibodies, or a data set of nucleic acid character strings encoding modified antibodies. To increase the diversity of any resulting recombinant nucleic acids, a second recombination step, in which the members of the library or the character strings in the data set are further recombined, is optionally performed. The one or more resulting recombinant nucleic acids is selected for a desirable trait or property, which results in first round selected nucleic acids or character strings. Typically, a third recombination step in which the first round selected nucleic acids or character strings are recombined with each other, or with one or more additional nucleic acid or character string, is performed. For example, the one or more additional nucleic acid of character string can correspond to the initial antibody gene, or to a library of nucleic acids such as a naïve or induced human library, e.g., to further evolve and/or humanize resulting second round recombined nucleic acids. Recursive rounds of recombination can be performed with any of the enumerated nucleic acids or character strings, or with any products of any round of recombination. Recombination is performed in vitro, in vivo, in silico or by a combination thereof.

Aspects of the present invention provide methods of evolving antibodies with increased affinity relative to a parental antibody. Such antibodies are the products of an ex vivo analog of the affinity maturation process. The invention also includes the coevolution of an antibody and its cognate antigen. A target antigen is selected and optimized for one or more properties. This optimized antigen can then be used to select among a population of diversified antibodies, with or without prior immunization of an animal host.

Another aspect of the invention provides methods for modifying antibody effector function. Features of the invention include Fc regions and antibodies comprising them, made by the methods of the invention. Antibody Fc regions can be enhanced in any of a number of respects including, for example, Fc receptor binding and complement component Clq binding.

In any case, resulting libraries, recombinant cells comprising one or more members of the libraries, computer readable media comprising data sets of interest and the like are, accordingly, features of the invention, as are kits comprising such elements. Kits optionally further comprise instructions for practicing the methods herein, containers for holding the materials, packaging elements, and the like.

The technology platform herein use expression cassettes which facilitate diversification, cloning and expression of antibody sequences. For example, the invention includes an Ig expression cassette. The cassette includes, e.g., one or more cloning sites for heavy chain (VH) and light chain (VL) sequences; an encoded N-terminal fusion of VH and VL with an stII, or other functional signal sequence; an encoded C-terminal fusion of VH and VL to human CH1 and a human CL regions; an encoded C-terminal fusion of VH and/or CH to a phage gIII protein; an amber stop codon at an antibody domain/gill border; and, a promoter such as a lacZ promoter, an alkaline phosphatase promoter, or an arabinose promoter. For example, the cassette can include a nucleic acid subsequence encoding a single-chain antibody (ScFv), a human kappa CL or a human lambda CL, or the like. In the cassette, the stII signal sequence provides periplasmic targeting, the C-terminal fusions of VH/CL to the phage gill protein provides for display on the surface of filamentous phage, the amber stop codon produces soluble antibody fragment in non-suppressing strains and the lacZ or other promoter provides inducible Ig gene expression in a host cell.

As noted, the invention provides a recombinant cell comprising the vector, and, optionally, other features which facilitate expression. For example, the vector can include one or more helper phage (e.g., a M13KO7 phage or a VCS-M13 phage). In one embodiment, the cell is a non-suppressing *E. coli* host such as strain W3110. Alternatively, expression of the recombinant nucleic acids of the invention can be in another bacterial cell, a yeast cell or a mammalian cell.

Libraries of recombinant cassettes containing a plurality of antibody sequences are also provided. The libraries can include, e.g., a plurality of expression cassettes as noted above, which include a plurality of different antibody encoding nucleic acids such as variants of one or more antibody parental nucleic acid.

Specific applications are also provided. For example, the invention includes methods of providing a population of diversified anti-enterotoxin monoclonal antibody nucleic acids. The methods include hybridizing a set of overlapping anti-enterotoxin monoclonal antibody nucleic acid fragments (e.g., synthesized oligonucleotides, nuclease digested nucleic acids, and the like) and elongating the set of hybridized overlapping anti-enterotoxin monoclonal antibody nucleic acid fragments. The set of overlapping anti-enterotoxin monoclonal antibody nucleic acid fragments can include, e.g., anti-*Staphylococcus* enterotoxin monoclonal antibody nucleic acid fragments, anti-Streptococcus enterotoxin monoclonal antibody nucleic acid fragments, and the like.

In one embodiment of the invention, the population of diversified anti-enterotoxin monoclonal antibody nucleic acids can be expressed to provide a variant anti-enterotoxin monoclonal antibody with desirable properties (e.g., a polyreactive antibody, a hyper-reactive antibody, etc.). In another embodiment, the diversified anti-enterotoxin monoclonal antibody nucleic acids can be introduced into a cell (e.g., an organism) and expressed to provide a variant anti-enterotoxin monoclonal antibody.

The methods can also include denaturing a population of diversified anti-enterotoxin monoclonal antibody nucleic acids, rehybridizing the denatured population, and extending the rehybridized population to provide a population of further diversified anti-enterotoxin monoclonal antibody nucleic acids. The steps of denaturing, rehybridizing, and extending can optionally be repeated. The population of further diversified anti-enterotoxin monoclonal antibody nucleic acids can also optionally be selected for efficient binding by an encoded anti-enterotoxin monoclonal antibody to at least one enterotoxin. The population of further diversified anti-enterotoxin monoclonal antibody nucleic acids can also be expressed to provide at least one further variant anti-enterotoxin monoclonal antibody (e.g., a polyreactive antibody, a hyper-reactive antibody, etc.).

DETAILED DISCUSSION

Definitions

Unless otherwise indicated, the following definitions supplement those in the art.

As used herein, an "antibody" refers to a protein comprising one or more polypeptides substantially or partially encoded by immunoglobulin genes or fragments of immunoglobulin genes, e.g., a fragment containing one or more complementarity determining region (CDR). The recognized immunoglobulin genes include the kappa, lambda, alpha, gamma, delta, epsilon and mu constant region genes, as well as myriad immunoglobulin variable region genes. Light chains are typically classified as either, e.g., kappa or lambda. Heavy chains are typically classified e.g., as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. In nature, each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2 (fragment antigen binding) and Fc (fragment crystallizable, or fragment complement binding). F(ab)'2 is a dimer of Fab, which itself is a light chain joined to VH-CH1 by a disulfide bond. The F(ab)'2 may be reduced under mild conditions to break the disulfide linkage in the hinge region thereby converting the (Fab')$_2$ dimer into an Fab' monomer. The Fab' monomer is essentially an Fab with part of the hinge region. The Fc portion of the antibody molecule corresponds largely to the constant region of the immunoglobulin heavy chain, and is responsible for the antibody's effector function (see, *Fundamental Immunology*, 4$^{th}$ edition. W.E. Paul, ed., Raven Press, N.Y. (1998), for a more detailed description of antibody fragments). While various antibody fragments are defined in terms of the digestion of an intact antibody, one of skill will appreciate that such Fab' or Fc fragments may be synthesized de novo either chemically or by utilizing recombinant DNA methodology, peptide display, or the like. Thus, the term antibody, as used herein also includes antibody fragments either produced by the modification of whole antibodies or synthesized de novo using recombinant DNA methodologies.

Antibodies also include single-armed composite monoclonal antibodies, single chain antibodies, including single chain Fv (sFv) antibodies in which a variable heavy and a variable light chain are joined together (directly or through a peptide linker) to form a continuous polypeptide, as well as diabodies, tribodies, and tetrabodies (Pack et al. (1995) *J Mol Biol* 246:28; *Biotechnol* 11:1271; and *Biochemistry* 31:1579). The antibodies are, e.g., polyclonal, monoclonal, chimeric, humanized, single chain, Fab fragments, fragments produced by an Fab expression library, or the like.

A "polyreactive" antibody is an antibody that can bind to more than one antigen, such as a bacterial toxin, e.g., from *Staphylococcus, Streptococcus*, and others.

A "hyper-reactive" antibody is an antibody that binds to an antigen with higher avidity or affinity than other antibodies.

The terms "humanized antibody molecule," or "humanized antibody," or "humanized immunoglobulin," are used interchangeably herein to refer to a molecule comprising an antigen binding site derived from one or more non-human immunoglobulins with at least a portion of the framework region of the light or heavy chain variable domain derived from one or more human immunoglobulins. A "humanized antibody" as used herein includes a humanized light chain variable domain immunoglobulin and a humanized heavy chain variable domain immunoglobulin. Optionally, the humanized antibody includes a constant region partially or wholly derived from (including synthetic analogs) one or more human gene sequence. A humanized antibody is expected to bind to the same target antigen as a donor antibody which supplied the CDRs. Typically, all segments or portions of the humanized antibody or immunoglobulin, with the exception of the CDRs, are substantially identical or substantially homologous to corresponding segments or portions of naturally occurring human immunoglobulin sequences. The humanized antibody typically has the structure of a naturally occurring antibody or a fragment of a naturally occurring antibody, e.g., a complete antibody, a ScFv antibody, a Fab fragment, a (Fab')$_2$ fragment, a light chain dimer, or a heavy chain dimer.

The term "chimeric" antibody is used to denote an antibody that is derived, typically through cloning methodologies, from more than one source or organism. Typically, large regions of sequence integrity are maintained through relatively simple cutting and pasting procedures that join polynucleotide sequences encoding, e.g., a murine, or other non-human variable region, such as a Fab fragment, with a human constant region, such as an Fc fragment.

Generation and Evolution of Therapeutic and Diagnostic Antibodies

Monoclonal (MAb) antibodies account for a significant portion of the U.S. market for biopharmaceuticals. Of the original biopharmaceuticals approved for sale in 1998, 30% were antibody-based (Biotechnology Information Institute, 1999). In fact, antibodies account for nearly 50% of all compounds currently in clinical trials (Wittrup, (1999) "Phage on display" *Tibtech* 17: 423-424. For convenience, antibody products can be grouped into at least five general classes, based upon their intended use or function. These classes are set forth below.

(1) Magic Bullets.

The first general class of antibody products are "magic bullets." These are primarily tumor-specific MAbs that arrest tumor growth by one of the following mechanisms: (a) Targeting tumor cells for destruction by antibody-dependent cell-mediated cytotoxicity (ADCC) or complement-mediated lysis (CML). One example is Rituxan (IDEC Pharmaceutical, Inc.), an anti-CD20 MAb for the treatment of Non-Hodgkins lymphoma (Scott (1998) "Rituximab: a new therapeutic monoclonal antibody for non-Hodgkin's lymphoma" *Cancer Pract* 6: 195-7). (b) A second example relates to antibodies which interfere with a critical component of tumor growth. Herceptin (Genentech, Inc.), an anti-HER-2 monoclonal antibody for treatment of metastatic breast cancer, is an example of an antibody with this mechanism of action (Baselga et al. (1998) "Recombinant humanized anti-HER2 antibody (Herceptin) enhances the antitumor activity of paclitaxel and doxorubicin against HER2/neu overexpressing human breast cancer xenografts [published erratum appears in *Cancer Res* (1999) 59(8):2020], *Cancer Res* 58: 2825-31). (c) A third example relates to antibodies for delivery of cytotoxic compounds (toxins, radionuclides, etc.) directly to a tumor or other site of interest. For example, One application Mab is CYT-356, a 90Y-linked antibody that targets radiation directly to prostate tumor cells (Deb et al. (1996) "Treatment of hormone-refractory prostate cancer with 90Y-CYT-356 monoclonal antibody" *Clin Cancer Res* 2: 1289-97. (d) A fourth application is antibody-directed enzyme prodrug therapy (ADEPT), where an enzyme co-localized to a tumor activates a systemically-administered pro-drug in the tumor vicinity. For example, Glaxo Wellcome Inc. is developing an anti-Ep-CAMI antibody linked to carboxypeptidase A for treatment of colorectal cancer (Wolfe et al. (1999) "Antibody-directed enzyme prodrug therapy with the T268G mutant of human carboxypeptidase A1: in vitro and in vivo studies with prodrugs of methotrexate and the thymidylate synthase inhibitors GW1031 and GW1843" *Bioconjug Chem* 10: 38-48).

(2) Antagonists.

The second general class of antibody products are antagonists. These MAbs are designed to specifically inhibit normal cellular functions for therapeutic benefit. An example is Orthoclone OKT3, an anti-CD3 MAb offered by Johnson and Johnson for reducing acute organ transplant rejection (Strate et al. (1990) "Orthoclone OKT3 as first-line therapy in acute renal allograft rejection" *Transplant Proc* 22: 219-20.

(3) Agonists.

The third general class of antibody products are agonists. These Mabs are designed to specifically enhance normal cellular functions for therapeutic benefit. For example, Genentech Inc. is developing Mab-based agonists of acetylcholine receptors for neurotherapy (Xie et al. (1997) "Direct demonstration of MuSK involvement in acetylcholine receptor clustering through identification of agonist ScFv" *Nat. Biotechnol.* 15: 768-71.

(4) Diagnostics.

The fourth general class of antibody products are diagnostic antibodies. There are many applications of MAbs to the field of diagnostics. With high target binding specificity, affordability and ease of use, antibodies are the reagents of choice for clinical diagnostics. Assays range from simple spot tests to more involved methods such as the radio-labeled NR-LU-10 MAb from DuPont Merck Co. used for tumor imaging (Rusch et al. (1993) "NR-LU-10 monoclonal antibody scanning. A helpful new adjunct to computed tomography in evaluating non-small-cell lung cancer." *J Thorac Cardiovasc Surg* 106: 200-4). In the research laboratory, MAbs are central reagents for ELISA, western blotting, immunochemistry, affinity chromatograpy methods and the like.

(5) Novel Functions.

The fifth general class of antibody products provide novel functions. The main antibodies in this group are catalytic antibodies such as Ig sequences that have been engineered to mimic the catalytic abilities of enzymes (Wentworth and Janda (1998) "Catalytic antibodies" *Curr Opin Chem Biol* 2: 138-44. For example, an interesting application involves using the catalytic antibody mAb-15A10 to hydrolyze cocaine in vivo for addiction therapy (Mets et al. (1998) "A catalytic antibody against cocaine prevents cocaine's reinforcing and toxic effects in rats" *Proc Natl Acad Sci USA* 95: 10176-81).

Antibody Diversification

Existing antibodies are not perfect drugs or diagnostic agents; they can have problems with low activity, undesirable side-effects, allergic reactions, low specificity, low avidity, or the like. Antibodies can be improved by (a) increasing the antigen binding affinity, thereby increasing therapeutic or diagnostic activity (b) increasing antigen binding specificity, thus reducing clinical side-effects and increasing diagnostic specificity, (c) decreasing the immunogenicity of the antibody molecule to avoid immune intolerance of therapeutics (e.g., by humanizing antibodies where the therapeutic use of the antibody occurs in a human patient), (d) increasing stability under a variety of in vitro buffer conditions, to regain activity after repeated cycles of denaturation and renaturation, to improve ease of preparation or to extend serum half-life in vivo, and (e) improving effector function of an antibody (e.g., by increasing complement activation or opsonization).

As a solution to these limitations, this invention provides a technology platform to clone Mabs specific to any given antigen and to employ diversification procedures, such as DNA shuffling, to improve their therapeutic and/or diagnostic potential. Mabs have an advantage over polyclonal antibodies in that Mabs provide consistent reagents that bind to specific epitopes with known binding affinities. Polyclonal antibody preparations contain a mixture of antibodies that bind to many different epitopes of the same antigen. This lack of binding specificity of polyclonal preparations makes them unsuitable for therapeutic use. However, certain features of the invention can also be applied to polyclonal antibody preparations Generating an Antibody Phage-Display Technology Platform Create Antibody Phage-display Vectors.

Construction and screening of antibody phage-display libraries is a well-established procedure with many possible variations (Griffiths and Duncan (1998) "Strategies for selection of antibodies by phage display" *Curr Opin Biotechnol* 9: 102-8; Hoogenboom et al. (1998) "Antibody phage display technology and its applications" *Immunotechnology* 4: 1-20). In the present invention, vectors that contain optimal combinations of useful features are provided. Specifically, vectors include a backbone containing the ampR gene and replication origin from pBR322 (Bolivar et al. (1977) "Construction and characterization of new cloning vehicles. II. A multipurpose cloning system" *Gene* 2: 95-113), the f1 origin for phage (Lorenzetti et al. (1985) "Plasmid pFCE4: a new system of *Escherichia coli* expression-modification vectors" *Gene* 39: 85-7), and an Ig expression cassette for Fab production.

The Ig expression cassette contains (a) cloning sites for heavy chain (VH) and light chain (VL) sequences, (b) N-terminal fusions of VH and VL with the stII signal sequence for periplasmic targeting (Chang et al. (1989) "Periplasmic secretion of human growth hormone by *Escherichia coli*" *Biochem Soc Trans* 17: 335-7) (c) C-terminal fusions of VH and VL to human CH1 and CL regions which provide stable Ig expression in *E. coli*, (d) C-terminal fusions of VH/CL to the phage gIII protein for monovalent display (Bass et al. (1990) "Hormone phage: an enrichment method for variant proteins with altered binding properties" *Proteins* 8: 309-14), (e) an amber stop codon at the Ab/gIII border to produce soluble Fab in non-suppressing strains, and (f) the lacZ promoter for inducible Ig gene expression (Messing et al. (1977) "Filamentous coliphage M13 as a cloning vehicle: insertion of a HindIII fragment of the lac regulatory region in M13 replicative form in vitro" *Proc Natl Acad Sci USA* 74: 3642-6).

An advantage of this Ig cassette lies in the fusions of VH and VL to known human CH1 and CL. Typically, fusions of variable regions to the constant domains of antibodies that are well-expressed in *E. coli* insures that the recombinant antibodies will also be highly expressed.

An additional advantage is when the donor species for the Fab library is not human, then human-chimeric Fabs are more desirable as human therapeutic agents than purely non-human Fabs (due to their decreased immunogenicity in humans). Variants of these vectors include (a) separate vectors containing the human kappa CL or the human lambda CL, (b) the alkaline phosphatase (AP) promoter to provide phosphate-limiting inducible expression (Kikuchi et al. (1981) "The nucleotide sequence of the promoter and the amino-terminal region of alkaline phosphatase structural gene (phoA) of *Escherichia coli*" *Nucleic Acids Res* 9: 5671-8), the arabinose (PBAD) promoter for quantitative gene induction (Guzman et al. (1995) "Tight regulation, modulation, and high-level expression by vectors containing the arabinose PBAD promoter" *J Bacteriol* 177: 4121-30), (c) a modified Ig cassette to express single-chain antibodies (scFv) (McCafferty et al. (1990) "Phage antibodies: filamentous phage displaying antibody variable domains" *Nature* 348: 552-4 or (d) a vector modified to encode a constant region comprising a Fc region that is the substrate for recombination. Other modification will be apparent to one of skill.

Additionally, phage displaying antibodies can be used to target and transfect mammalian cells with packaged DNA encoding a variety of functions. Barry et al. proposed (1996) *Nature Med* 2:229, that isolated phage displaying specific targeting peptides direct DNAs to target cells. Antibodies are more effective than peptides for this purpose as they typically bind to their target, e.g., a cell to be transfected, with higher affinity than do targeting peptides.

Choosing an Appropriate Target Antigen.

The choice of a target antigen is made based upon any available criteria, such as the existence of an antigen target on a cell. For example, to isolate novel MAbs for cancer immunotherapy, a human tumor-specific antigen is chosen as an antigen target. Selection criteria include specificity of the antigen to tumor cells, availability/stability of purified antigen and the like. Further details are found herein, e.g., in "Additional Details Regarding Antibody and Target Selection."

Choose Source of Lymphatic Tissue.

Animals (e.g., mouse, hamster, rabbit, chicken) are a logical source of anti-human antibodies, since their immune systems recognize human proteins as foreign. Many diagnostic MAbs are derived from animal Ig sequences. However, such antibodies retain characteristic animal sequences which may elicit adverse reactions when used as human therapeutics. Immunization of non-human primates, such as monkeys offers the potential advantage of generating a repertoire of nearly human high affinity antibodies. An alternative approach is to isolate fully-human Mabs from large libraries of naïve (non-immunized) human donors. If the library is sufficiently diverse, MAbs against many self-antigens can be routinely isolated (Griffiths et al. (1993) "Human anti-self antibodies with high specificity from phage display libraries" *Embo J* 12: 725-34; Vaughan et al. (1996) "Human antibodies with sub-nanomolar affinities isolated from a large non-immunized phage display library" [see comments]. Nat Biotechnol 14: 309-14.)

Isolating Total mRNA from Lymphocyte Tissue.

The spleen is a convenient source of animal tissue while peripheral blood mononuclear cells (PBMC) are good sources of human tissue (Marks et al. (1991) "By-passing immunization. Human antibodies from V-gene libraries displayed on phage" *J Mol Biol* 222: 581-97) or bone marrow (Vaughan et al. (1996) "Human antibodies with sub-nanomolar affinities isolated from a large non-immunized phage display library" [see comments]. *Nat Biotechnol* 14: 309-14).

Amplify VH and VL Sequences by RT-PCR.

Using DNA sequence alignments of Igs, primers are designed to amplify human (Tomlinson (1991) *Immunoglobulin genes*. Academic Press, London), mouse (Clackson et al. (1991) "Making antibody fragments using phage display libraries" *Nature* 352:624-8; Yamanaka et al. (1995) "An improved phage display antibody cloning system using newly designed PCR primers optimized for Pfu DNA polymerase" *J Biochem* (Tokyo) 117: 1218-27), chicken (Davies et al. (1995) "Selection of specific phage-display antibodies using libraries derived from chicken immunoglobulin genes" *J Immunol Methods* 186: 125-35; Yamanaka et al. (1996) "Chicken monoclonal antibody isolated by a phage display system" *J Immunol* 157: 1156-62) or other available genes.

Clone VH and VL Sequences into the Phase Display Vector.

Independent insertion sites for VH and VH sequences creates combinatorial diversity of heavy and light chains.

Transform *E. coli.*

Library diversity can be limited by transformation efficiency. However, electroporation of cells can routinely yield >1×10$^9$ transformants per microgram of DNA (Sharma and Schimke (1996) "Preparation of electrocompetent *E. coli* using salt-free growth medium" *Biotechniques* 20: 42-4). For example, *E. coli* strain XL1-Blue is an appropriate strain to tranform as it has the supE44 mutation that allows readthrough of the amber stop codon to create gIII fusions.

Add Helper Phase to Produce Mature Fab-phage Libraries

If wild-type (M13KO7 or VCS-M13) helper phage are used, then over 90% of rescued phage contain wild-type gIII, and therfore display no Fabs (Vieira and Messing (1987) "Production of single-stranded plasmid DNA" *Methods Enzymol* 153: 3-11. However, any Fabs that are displayed will be monovalent; this is helpful when selecting for antibodies with increased binding affinities (Garrardet al. (1991) "Fab assembly and enrichment in a monovalent phage display system" *Biotechnology* 9: 1373-7.

If monovalent display is not used, then the effective diversity of the library can be increased by using a helper phage with a deleted gIII, thus insuring that every rescued phage will display FAb (Rakonjacet al. (1997) "Filamentous phage infection-mediated gene expression: construction and propagation of the gIII deletion mutant helper phage R408d3" *Gene* 198: 99-103).

Pan Fab-Phage Library Against the Antigen.

Typically, the antigen is affixed to plasticware such as immunotubes or microtiter plates (Kretzschmar et al. (1995) "Selection procedures for nonmatured phage antibodies: a quantitative comparison and optimization strategies" *Anal Biochem* 224: 413-9), or ELISA plates (Barbas and Burton (1996) "Selection and evolution of high-affinity human antiviral antibodies" *Trends Biotechnol* 14: 230-4. If the supply of antigen is not limiting, more efficient selection can be performed by affinity chomatography (Bass et al. (1990) "Hormone phage: an enrichment method for variant proteins with altered binding properties" *Proteins* 8: 309-14).

Isolate and Characterize Positive Clones.

Plasmid DNA from positive clones, identified in a phage screen is isolated and transformed into a non-suppressing *E. coli* host (eg W3110). Without the a sup mutation, translation terminates at the amber stop codon and free Fab is produced. Soluble Fab is prepared and tested for specific binding to the original antigen by standard ELISA methods. DNA from positive clones is sequenced to determine the uniqueness of each clone; after multiple rounds of panning, e.g., against purified antigen, cells or whole tissues, up to greater than 90% of recovered clones will share the same sequence (Barbas et al. (1993) "Molecular profile of an antibody response to HIV-1 as probed by combinatorial libraries" *J Mol Biol* 230: 812-23. Depending on the application, further tests can be conducted, such as measuring antigen-binding affinities by surface plasmon resonance (Alfthan (1998) "Surface plasmon resonance biosensors as a tool in antibody engineering" *Biosens Bioelectron* 13: 653-63, epitope mapping by scanning mutagenesis (Cunningham and Wells (1989) "High-resolution epitope mapping of hGH-receptor interactions by alanine-scanning mutagenesis" *Science* 244: 1081-5; Balint and Larrick (1993) "Antibody Engineering by Parsimonious Mutagenesis" *Gene* 137:109-118), or ex vivo neutralization tests (Laal et al. (1993) "A rapid, automated microtiter assay for measuring neutralization of HIV-1" *AIDS Res Hum Retroviruses* 9: 781-5).

Directed Evolution of Monoclonal Antibodies for Improved Detection and Neutralization of Bacterial Enterotoxins The present invention can include providing monoclonal antibodies, e.g., against the *Staphylococcus* and *Streptococcus* enterotoxins which can be optimized via a variety of diversification procedures, including among many others DNA shuffling, e.g., as diagnostic and/or immunotherapeutic agents. For example, in the military sector (e.g., the Department of Defense (DOD), Defense Advanced Research Projects Agency (DARPA), etc.) there is a need for rapid and accurate diagnosis of potential biological warfare agents, such as the *Staphylococcus* and *Streptococcus* enterotoxins. In one embodiment, monoclonal antibodies, including the improved monoclonal antibodies of the invention, can be combined with appropriate hardware, e.g., a hand-held Biacore device, such as the one being investigated by A. Barraud at the Centre d'Etudes Nucleaires de Saclay, France, an antibody-based fiber-optic biosensor device like the one developed by Geo-Centers Inc. (Fort Washington, Mass.) that provides rapid and sensitive results, and the like. Improved diagnostics for enterotoxins are useful both for civilian and military purposes. Furthermore, antibodies like those generated against enterotoxins can be humanized and evaluated as immunotherapeutic agents for the treatment of sepsis.

Monoclonal antibodies are available (e.g., from Research Diagnostics Inc., Igen International Inc., etc.) that recognize some *Staphylococcus aureus* enterotoxin groups. Additionally, polyclonal antibodies have been used in ELISAs to detect toxins from specific groups. These or other pre-existing antibodies, or any novel antibodies can be optimized by the recombination and mutagenesis, e.g., nucleic acid shuffling, methods disclosed herein. For example, the diversified, e.g., shuffled, antibodies of the invention can be selected to be more polyreactive (i.e., binding to toxins from all of the major groups) and more reactive, or hyper-reactive (i.e., binding to antigens with higher affinity). Polyreactive monoclonal antibodies can provide value in that fewer unique antibody clones are necessary, e.g., to detect and/or neutralize known enterotoxins. Hyper-reactive monoclonal antibodies can provide value in terms of increased sensitivity of each assay or therapeutic application.

Chimeric proteins can be generated by a variety of recombination and mutagenesis procedures, such as nucleic acid shuffling, e.g., enterotoxin gene families (e.g., *Staphylococcus* groups A, B, C, D, E, G, H, I, J, TSST-1, *Streptococcus* groups A, B, and C, and the like) which, in turn, can be used as vaccines to provide protection against challenges from multiple enterotoxin groups. Lymphocytes from vaccinated mice can be isolated, the IgG sequences can be cloned into a phage-display vector, and the resulting libraries can be panned against the chimeric toxins. Polyreactive clones can be selected and thereafter, further diversified to improve their binding properties. See e.g., Crameri et al. (1996) "Construction and Evolution of Antibody-Phage Display Libraries by DNA Shuffling," Nat. Med. 2:100. Advantages of this approach include that the antibody phage display produces monoclonal antibodies that are superior to polyclonals in terms of reproducibility of activity and production cost. Furthermore, DNA diversification and selection procedures, e.g., shuffling, can significantly improve the binding properties of antibodies and the selected monoclonals can serve as proprietary clones.

Testing the System by Cloning MAbs Specific to HBsAg, *Yersinia* V Antigen and Staph/Strep Enterotoxins.

MAbs specific to HBsAg, *Yersinia* V antigen, and *Staph*/Strep enterotoxins are optimized by DNA diversification and selection. MAbs specific to each antigen or antigen variant provides new and useful reagents for epitope mapping, affinity purification, neutralization tests, ELISAs and western analysis. In addition, a convenient and reliable source of immunized donor tissue is produced by mice vaccination studies of the variant antibodies.

DNA vaccines have the advantage that an isolated gene can be used for immunization, without requirement for the protein. However, the B-cell responses are often weak (Laylor et al. (1999) "DNA vaccination favours memory rather than effector B cell responses" *Clin Exp Immunol* 117: 106-12) and are difficult to measure by conventional methods. As the HBsAgs are tested by DNA vaccination, phage display is a powerful new system to characterize antibody responses induced by genetic vaccines. In addition, this provides a rapid means to generate new MAbs against proteins when only the DNA sequences are available.

Directed Evolution of Monoclonal Antibodies

DNA Diversification Strategies.

The strength of binding of an antibody to its cognate antigen is referred to as its "affinity." Affinity maturation is usually thought of as the increase in affinity of an immune response upon subsequent doses of an immunogen. In nature, it reflects the somatic mutation of variable gene sequences of individual antigen-stimulated B cells followed by selection and clonal expansion of those B cells bearing higher-affinity antigen receptors.

The methods of the present invention provide for an ex vivo analog of affinity maturation. For example, various DNA shuffling and/or additional diversification procedures are highly efficient forms of hypermutation, which unlike the process observed in vivo, are not restricted to so-called hypervariable regions. Diversity, or hypermutation resulting from, e.g., the shuffling process provides the substrate for an artificial selection process. In cases where the selection criteria include increased affinity relative to a parental antibody, or to a reference standard of binding, affinity maturation is, in essence, achieved.

For example, a first step towards improving antibody binding affinities involves chain shuffling, where the VH or VL gene of the parent antibody is replaced with a complete V-gene repertoire and re-selected (Schier and Marks (1996) "Efficient in vitro affinity maturation of phage antibodies using BIAcore guided selections" *Hum Antibodies Hybridomas* 7: 97-105). The DNA diversification and selection procedures described herein are an improvement of this process in that they create additional diversity by randomly inserting V-gene fragments (as well as any other antibody or antibody homologue subsequence) into the parental gene framework.

Alternatively, effector function of an antibody can be modified and/or optimized by recombination and/or mutagenesis of the heavy chain constant, or Fc regions. Recombinant Fc sequences can be assayed directly in a complex, functional assay, e.g., whole animal pathogenic challenge, or by using in vitro model systems such as antibody-based neutralization, or complement mediated lysis assays.

Antibody encoding polynucleotides are optionally used as substrates for a variety of recombination and recursive recombination (e.g., DNA shuffling) reactions. A variety of diversity generating protocols, including nucleic acid shuffling protocols, are available and fully described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive.

Indeed, the various methods can be used singly or in combination, in parallel or in series, to access diverse sequence variants.

The result of any of the diversity generating procedures described herein can be the generation of one or more nucleic acids, which can be selected or screened for nucleic acids that encode proteins with or which confer desirable properties. Following diversification by one or more of the methods herein, or otherwise available to one of skill, any nucleic acids that are produced can be selected for a desired activity or property, e.g. increased affinity or specificity, reduced immunogenicity of the encoded antibody. This can include identifying any activity that can be detected, for example, in an automated or automatable format, by any of the assays in the art, e.g., by ELISA, Biacore plasmon resonance, immunodiffusion, immunoprecipitation, affinity column purification, etc. A variety of related (or even unrelated) properties can be evaluated, in serial or in parallel, at the discretion of the practitioner.

Descriptions of a variety of diversity generating procedures, including recursive recombination procedures, e.g., shuffling, and/or methods which can be incorporated into such procedures, for generating modified nucleic acid sequences encoding antibodies are found the following publications and the references cited therein: Stemmer, et al. (1999) "Molecular breeding of viruses for targeting and other clinical properties" *Tumor Targeting* 4:1-4; Ness et al. (1999) "DNA Shuffling of subgenomic sequences of subtilisin" *Nature Biotechnology* 17:893-896; Chang et al. (1999) "Evolution of a cytokine using DNA family shuffling" *Nature Biotechnology* 17:793-797; Minshull and Stemmer (1999) "Protein evolution by molecular breeding" *Current Opinion in Chemical Biology* 3:284-290; Christians et al. (1999) "Directed evolution of thymidine kinase for AZT phosphorylation using DNA family shuffling" *Nature Biotechnology* 17:259-264; Crameri et al. (1998) "DNA shuffling of a family of genes from diverse species accelerates directed evolution" *Nature* 391:288-291; Crameri et al. (1997) "Molecular evolution of an arsenate detoxification pathway by DNA shuffling," *Nature Biotechnology* 15:436-438; Zhang et al. (1997) "Directed evolution of an effective fucosidase from a galactosidase by DNA shuffling and screening" *Proc. Natl. Acad. Sci. USA* 94:4504-4509; Patten et al. (1997) "Applications of DNA Shuffling to Pharmaceuticals and Vaccines" *Current Opinion in Biotechnology* 8:724-733; Crameri et al. (1996) "Construction and evolution of antibody-phage libraries by DNA shuffling" *Nature Medicine* 2:100-103; Crameri et al. (1996) "Improved green fluorescent protein by molecular evolution using DNA shuffling" *Nature Biotechnology* 14:315-319; Gates et al. (1996) "Affinity selective isolation of ligands from peptide libraries through display on a lac repressor 'headpiece dimer'" *Journal of Molecular Biology* 255: 373-386; Stemmer (1996) "Sexual PCR and Assembly PCR" In: *The Encyclopedia of Molecular Biology*. VCH Publishers, New York. pp. 447-457; Crameri and Stemmer (1995) "Combinatorial multiple cassette mutagenesis creates all the permutations of mutant and wildtype cassettes" *BioTechniques* 18:194-195; Stemmer et al., (1995) "Single-step assembly of a gene and entire plasmid form large numbers of oligodeoxyribonucleotides" *Gene,* 164:49-53; Stemmer (1995) "The Evolution of Molecular Computation" *Science* 270: 1510; Stemmer (1995) "Searching Sequence Space" *Bio/Technology* 13:549-553; Stemmer (1994) "Rapid evolution of a protein in vitro by DNA shuffling" *Nature* 370:389-391; and Stemmer (1994) "DNA shuffling by random fragmentation and reassembly: In vitro recombination for molecular evolution." *Proc. Natl. Acad. Sci. USA* 91:10747-10751.

Mutational methods of generating diversity include, for example, site-directed mutagenesis (Ling et al. (1997) "Approaches to DNA mutagenesis: an overview" *Anal Biochem.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D.M.J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" *Science* 242:240-245); oligonucleotide-directed mutagenesis (*Methods in Enzymol.* 100: 468-500 (1983); *Methods in Enzymol.* 154: 329-350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487-6500; Zoller & Smith (1983) "Oligonucleotide-directed mutagenesis of DNA fragments cloned into M13 vectors" *Methods in Enzymol.* 100: 468-500; and Zoller & Smith (1987) "Oligonucleotide-directed mutagenesis: a simple method using two oligonucleotide primers and a single-stranded DNA template" *Methods in Enzymol.* 154:329-350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749-8764; Taylor et al. (1985) "The rapid generation of oligonucleotide-directed mutations at high frequency using phosphorothioate-modified DNA" *Nucl. Acids Res.* 13: 8765-8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679-9698; Sayers et al. (1988) "Y-T Exonucleases in phosphorothioate-based oligonucleotide-directed mutagenesis" *Nucl. Acids Res.* 16:791-802; and Sayers et al. (1988) "Strand specific cleavage of phosphorothioate-containing DNA by reaction with restriction endonucleases in the presence of ethidium bromide" *Nucl. Acids Res.* 16: 803-814); mutagenesis using gapped duplex DNA (Kramer et al. (1984) "The gapped duplex DNA approach to oligonucleotide-directed mutation construction" *Nucl. Acids Res.* 12: 9441-9456; Kramer & Fritz (1987) *Methods in Enzymol.* "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987-6999).

Additional suitable methods include point mismatch repair (Kramer et al. (1984) "Point Mismatch Repair" *Cell* 38:879-887), mutagenesis using repair-deficient host strains (Carter et al. (1985) "Improved oligonucleotide site-directed mutagenesis using M13 vectors" *Nucl. Acids Res.* 13: 4431-4443; and Carter (1987) "Improved oligonucleotide-directed mutagenesis using M13 vectors" *Methods in Enzymol.* 154: 382-403), deletion mutagenesis (Eghtedarzadeh & Henikoff (1986) "Use of oligonucleotides to generate large deletions" *Nucl. Acids Res.* 14: 5115), restriction-selection and restriction-selection and restriction-purification (Wells et al. (1986) "Importance of hydrogen-bond formation in stabilizing the transition state of subtilisin" *Phil. Trans. R. Soc. Lond. A* 317: 415-423), mutagenesis by total gene synthesis (Nambiar et al. (1984) "Total synthesis and cloning of a gene coding for the ribonuclease S protein" *Science* 223: 1299-1301; Sakamar and Khorana (1988) "Total synthesis and expression of a gene for the a-subunit of bovine rod outer segment guanine nucleotide-binding protein (transducin)" *Nucl. Acids Res.* 14: 6361-6372; Wells et al. (1985) "Cassette mutagenesis: an efficient method for generation of multiple mutations at defined sites" *Gene* 34:315-323; and Grundström et al. (1985) "Oligonucleotide-directed mutagenesis by microscale 'shotgun' gene synthesis" *Nucl. Acids Res.* 13: 3305-3316), double-strand break repair (Mandecki (1986); *Arnold* (1993) "Protein engineering for unusual environments" *Current Opinion in Biotechnology* 4:450-455. "Oligonucleotide-directed double-strand break repair in plasmids of *Escherichia coli*: a method for site-specific mutagenesis" *Proc. Natl. Acad. Sci. USA,* 83:7177-7181). Additional details on many of the above methods can be found in *Methods in Enzymology* Volume 154, which also describes useful controls for troubleshooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al. filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Mar. 2, 2000 (U.S. Ser. No. 60/186,482).

In brief, several different general classes of sequence modification methods, such as mutation, recombination, etc., are applicable to the production of antibodies with improved and desired properties, and set forth, e.g., in the references above.

The following exemplify some of the different types of preferred formats for diversity generation in the context of the present invention, including, e.g., certain recombination, and recursive recombination, based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) *Proc. Natl. Acad. Sci. USA* 91:10747-10751. Thus, nucleic acids encoding antibodies, antibody fragments, and the like, are fragmented and recombined in vitro based on sequence similarity, and then selected for the property of interest.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Thus, in vivo recombination methods can be employed to generate antibodies with desired properties, for example by transfecting libraries of ScVF antibody encoding nucleic acids into a population of host cells, where they are recombined and expressed for selection.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202); "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579).

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) "METHODS OF POPULATING DATA STRUCTURES FOR USE IN EVOLUTIONARY SIMULATIONS" by Selifonov and Stemmer (PCT/US00/01138), filed Jan. 18, 2000; and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579). Extensive details regarding in silico recombination methods are found in these applications. This methodology is generally applicable to the present invention in providing for recombination of antibody encoding sequences in silico and/or the generation of corresponding nucleic acids or proteins.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "SINGLE-STRANDED NUCLEIC ACID TEMPLATE-MEDIATED RECOMBINATION AND NUCLEIC ACID FRAGMENT ISOLATION" by Affholter, U.S. Ser. No. 60/186,482, filed Mar. 2, 2000.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial a library of variants which can optionally serve as a substrate for one or more in vitro or in vivo recombination methods. See, also, Ostermeier et al. (1999) "Combinatorial Protein Engineering by Incremental Truncation," *Proc. Natl. Acad. Sci. USA*, 96: 3562-67; Ostermeier et al. (1999), "Incremental Truncation as a Strategy in the Engineering of Novel Biocatalysts," *Biological and Medicinal Chemistry*, 7: 2139-44.

Mutational methods which result in the alteration of individual nucleotides or groups of contiguous or non-contiguous nucleotides can be favorably employed to introduce nucleotide diversity into the antibody sequences of the present invention. Many mutagenesis methods are found in the above-cited references; additional details regarding mutagenesis methods can be found in following, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11-15 and Caldwell et al. (1992) *PCR Methods Applic.* 2:28-33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science*, 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811-7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548-1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see, Short (1999) U.S. Pat. No. 5,958,672 "PROTEIN ACTIVITY SCREENING OF CLONES HAVING DNA FROM UNCULTIVATED MICROORGANISMS"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "PRODUCTION OF ENZYMES HAVING DESIRED ACTIVITIES BY MUTAGENESIS." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods can be applied to the present invention as well.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation, and combinations of recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

The recombining steps can be performed in vivo, in vitro, or in silico as described in more detail in the references above. Also included in the invention is a cell containing any resulting recombinant nucleic acid, nucleic acid libraries produced by recursive recombination of the nucleic acids set forth herein, and populations of cells, vectors, viruses, plasmids or the like comprising the library or comprising any recombinant nucleic acid resulting from recombination (or recursive recombination) of a nucleic acid as set forth herein with another such nucleic acid, or an additional nucleic acid. Corresponding sequence strings in a database present in a computer system or computer readable medium are a feature of the invention.

To maximize the probability of recovering beneficial recombinants, several variations of recombination and mutagenesis procedures can be compared. Such variations include (a) recombining only positive clones (e.g., low-diversity shuffling), (b) recombining positive clones with all clones from the parent library (e.g., high-diversity shuffling), (c) recombining positive clones with other members of the Ig super family, for example with T cell receptor genes (e.g., family shuffling), especially, e.g., where added functionality is desirable (e.g., in providing antibodies with unique functions such as enzymatic activity) (d) spiking the recombination reaction with oligos encoding partially-randomized CDRs (Crameriet al. (1996) "Construction and evolution of antibody-phage libraries by DNA shuffling" *Nat Med* 2: 100-2), (e) serial passage of recombinant, e.g., shuffled, clones through an *E. coli* mutator strain (e.g. *E. coli* mutD5) (Low et al. (1996) "Mimicking somatic hypermutation: affinity maturation of antibodies displayed on bacteriophage using a bacterial mutator strain" *J Mol Biol* 260: 359-68) (f) recombining, e.g., shuffling, clones derived from a second functionally related library, (g) combining recombination, e.g., shuffling, techniques with standard cloning and mutagenesis techniques, by including recombinant DNA molecules produced by any standard technique among the nucleic acids being diversified, e.g., shuffled. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471-476) prior to DNA recombination, e.g., shuffling, according to any of the methods described herein, or (h) any combination of the above.

Additional Details Regarding Antibody and Target Selection

The methods of the present invention can readily be applied to the development and optimization of antibodies to fulfill a wide variety of functions, determined largely by the selection of the target antigen or antigens. It is possible through the selection of appropriate target antigens to generate and evolve antibodies as treatment candidates for a number of human diseases. For example diseases which result from a disregulation of the immune system, such as chronic inflammatory diseases, (e.g., lupus erythematosus, rheumatoid arthritis, and diabetes) and allergies, can respond favorably to antibodies which target components of the immune regulatory network, e.g., T cell and B cell surface determinants, superantigens, MHC class II, interferon gamma, alpha interferon, and leucointegrin. The invention also provides for the development of optimized and humanized antibody reagents for the treatment of acute autoimmune disorders such as rhesus factor induced hydrops fetalis through the generation of improved recombinant anti-rh antibodies.

In addition, antibodies directed against other targets, such as markers isolated from vascular endothelium or activated epithelium, have potential in modulating the immune response. Similarly, antibodies to small molecule immunemodulators, such as nitrotyrosine, can play a role in regulating immune system disorders. Antibodies raised and optimized against allergens, for example, dust mite allergen, offer a potential therapeutic agent in the treatment of common allergies.

Novel and improved antibodies directed against Lymphocyte cell surface receptors and ligands (e.g., B7, CD80, CD86, CD28, and CTLA-4), Adhesion Molecules (e.g., LFA-1, Pgp-1, VLA-4, VCAM-1, ICAM-1, etc.), interleukins and their receptors (e.g., 11-2, IL-2R, etc.), cytokines (interferon-gamma, tumor necrosis factor, alpha interferon, transforming growth factor-beta, etc.), are all a feature of the invention. Likewise, antibodies against Cluster of Differentiation (CD) antigens, for example: CD25, CD20, CD28, CD18, CD23, CD22, CD30, CD44, CD150 and their receptors, e.g., CD45R, are all suitable substrates for the methods of the invention.

The present invention also provides for the derivation and evolution of novel cancer immunotherapeutic agents as noted supra. Pan carcinoma markers as well as markers expressed on the surface of specific tumor types, e.g., bladder, breast, prostate, ovary, melanoma, glioma, lymphoma, and colorectal carcinoma, etc. can be isolated and used as described herein to generate monoclonal antibodies. Similarly, well known tumor growth factors, regulatory molecules, and markers including TNF-alpha, interferon gamma, ras, ErbB2, ErbB-3 R, adrenomedulin, Fas, EGF, EGF-R, rat neuT, Flk-1 receptor, vascular endothelial growth factor (VEGF), nsclc, pancarcinoma markers, carcinoembryonic antigen, (CEA), human chorionic gonadotrophin (HCG), alphafetoprotein (AFP) are all suitable as targets for the antibodies of the invention.

Neurological disorders such as Alzheimers disease can be addressed using the methods and antibodies of the invention, for example by developing optimized antibodies against beta-amyloid aggregates. Antibodies useful in the treatment of such chronic degenerative disorders as Multiple Sclerosis can be developed using antibodies selected by the methods of the invention to stimulate remyelination. Antibodies of the invention can also be optimized for use in the treatment of drug overdose, and toxicity, e.g., cocaine, antidepressents. Reagents useful for the diagnosis of neurological disorders are also a feature of the invention. For example antibodies directed against neural components, such as HexosaminidaseA are valuable in the diagnosis of specific neurological disorders, e.g., Tay-Sachs disease.

Humanized antibodies optimized to bind proteins involved in lipid homeostasis, such as Cholesterol ester transfer protein (CETP), low density lipoprotein (LDL), and the atherosclerotic plaque marker, Z2D3, can readily be made by the methods of the invention, and have potential utility in the treatment of diagnosis and treatment of hyperlipidemia and arteriosclerosis. Similarly, antibodies to human adipocytes have potential in the treatment of obesity. Antibodies developed by the methods of the invention and directed against Type II phospholipase A2 are a possible reagent in the treatment of myocardial infarction, and antibodies against fibring have potential in the treatment of clotting disorders.

The present invention also provides for antibodies useful in the treatment of infectious diseases, including those caused by viral pathogens, e.g., Herpes Simplex Virus, Herpes zoster, Hepatitis, A, B, C, Cytalomegalovirus, Respiratory syncitial virus, rabies, Human Papilloma Virus, Varicella zoster, B19 Parvovirus and viral agents causing the common cold, among others. An aspect of the invention relates to the coevolution of antibodies against HIV, inlcuding epitopes derived from envelope proteins, and including p17, gp120, gp41, p24. Antibodies can also be developed that are useful in the treatment of infectious diseases caused by bacterial agents, including enterococci, (e.g., *E. coli* verotoxin), *Bacillus psocyaneus* (flagellum), *Pneumocystis carinii, Pseudomonas aureuginosa, Staphylococcus epidermidis, Clostridium difficile, Cryptosporidium* sp., *Pseudomonas* sp., and tetanus. Candidates for the treatment of fungal infections include ubiquitous heat shock proteins, e.g., the hsp90 of *Candida albicans*, which can be selected for high affinity binding, in spite of the limited antigenicity of the target antigen.

In addition to antibodies useful in the treatment or diagnosis of specific disorders as enumerated above, and further enumerated in Tables 1 and 2, it will be clear that such various subsets of antibody classes as anti-idiotype antibodies, mimetic antibodies, anti-codon antibodies, bifunctional antibodies, diabodies, tribodies, tetrabodies, single chain antibodies, single-arm composite antibodies, monovalent antibodies, humanized antibodies, primatized antibodies, Trigger antibodies, antibody aggregates, and antibody-conjugates are all features of the invention. Antibody-conjugates include antibodies conjugated to protein moieties, (e.g., enzymes, nerve growth factor), chemotherapeutic or antiproliferative agents, (genistein, doxorubicin, calicheamicin, MX-DPTA, maytansine, mitomycin, etc.), radio-conjugates, (e.g., rhenium-186, rhenium-188, astatine-211, technetium-99, indium-111) and toxins, (e.g., PE38 and PE40 truncated *Pseudomonas* exotoxin, blocked ricin). Also included are antibodies conjugated to bioactive moieties such as vasoactive agents, and moieties which facilitate transport of the antibody across membranes or into the nucleus. In addition, antibodies conjugated to non-biological particles such as gold, and magnetic nanoparticles (MNP, e.g., ranging from 10-50 nm in size) are a feature of the invention.

Tables 1 and 2, below, provides a description of a variety of antibodies, their origins, source, target or diagnostic use, and, if available, accession number. In Table 1, the H column relates to whether the antibodies are humanized. Any of the antibodies in the Tables, as well as any of those noted herein, can be modified according to the methods of the invention. For example, the antibodies can be diversified and selected, e.g., shuffled, to improve activity, or specificity, to reduce immunogenicity (e.g., by humanization) or the like. In Table 1, the majority of antibodies are monclonal antibodies, although some of those presented are polyclonal. The present invention relates to the diversification, for example, by nucleic acid shuffling, of both monoclonal and polyclonal antibodies, and polyclonal antibodies can be converted to polyclonal antibodies by standard methods.

One aspect of the invention provides methods of improving an antibody of Table 1 or Table 2. In the methods, a nucleic acid encoding an antibody of Table 1 or 2, or a homologue or fragment thereof is recombined with one or more additional antibody coding nucleic acid, or homologue or fragment thereof. A fragment of a sequence for purposes of this disclosure is an actual fragment produced, e.g., by nuclease digestion (e.g., DNAse digestion), mechanical shearing, amplification, etc., of the indicated parental nucleic acid, or an oligonucleotide generated to include at least about 20, and typically about 40 or more nucleotides of the parental nucleic acid. In many recombination procedures noted in detail supra, parental nucleic acids such as the nucleic acids encoding the enumerated nucleic antibodies above, are fragmented, hybridized with homologous nucleic acid fragments and the resulting hybridized nucleic acids extended using a polymerase. Other approaches such as in silico sequence recombination (in silico shuffling) and whole genome recombination (whole genome shuffling) (e.g., in conjunction with libraries of the relevant nucleic acids) can also be adopted.

In addition to the enumerated antibodies, other antibodies generated against, e.g., the targets used to generate the antibodies of Table 1 and 2, can also be used to generate new antibodies with similar activities. These antibodies are also desirably diversified (e.g., shuffled) using the techniques herein.

In one embodiment, antibodies are produced using naïve libraries of human antibodies or from cells isolated from humans which are immunized with a target of interest (e.g., cells isolated from patients suffering from a disease such as HIV infection or any other condition which results in production of antibodies to a target). For example, any of the relevant targets can be used to screen naïve libraries of displayed antibodies (e.g., naïve human libraries). Alternatively, the targets can be used to elicit antibodies in animals such as mice or rabbits using standard methods (see, the references cited herein).

TABLE 1

| Name | Origin | H | Source | Target | Acc/# | Note |
|---|---|---|---|---|---|---|
| 2930 | | | Invitron | diagnostic | | |
| (+aminoterin) | | | Cytogen | cancer | | |
| (+doxorubicin) | | | Suzlou Medical Inst., China | RNA synthesis inhibito | | |
| (+modified diphtheria toxin) | | | Research Corporation Technologie | cancer | | |
| (+superantigen) | | | Active Biotech | cancer, other | | |
| (+technetium-99-) | mu | | Immunomedics | cancer, diagnostic | | |
| (BI-P-A) anti-myosin + radiolabel | | | Centocor | myocardial infarction imaging | | |
| 1209W95 | | | GlaxoWellcome | prostate, lung, gastric Ca. | | |
| 145-2.C11 | | | Hoechst Marion Roussel | GvHD | | |
| 14F7 | | | Center for Molecular Immunology | cancer, imaging agent | | |
| 17-1A | mu | | Centocor | cancer | | |
| 1A3 | | | Invitron | cancer | | |
| 1A3 | mu | | Washington Univ. School of Medicine | cancer | | |
| 1F7 | | | Immpheron | HIV, infection | | |
| 28-19-8 | mu | | Eli Lilly | carcinoembryonic antigen | | |
| 28A32 | hu | | Akzo Nobel | cancer, imaging agent | | |
| 2A11 | | | Hybritech | cancer | | |
| 2B-1 | mu | | Chiron | c-erbB-2/CD16 | | bispecific |
| 2B5 | | | Temple Univ. | plasma kininogen | | |
| 2F5 | hu | | Merck | gp41 | | |
| 2G4 | | | Invitron | diagnostic | | |
| 33B3.1 | mu | | Pastuer Merieux | IL-2 receptor | | |
| 3622W94 | | | GlaxoWellcome | prostate, lung Ca. | | |
| 3C2 | | | Invitron | diagnostic | | |
| 3C9 | | | IDEC | AIDS vaccine | | |
| 3F8 | | | Sloan-Kettering | tumors, neuro; mel. | | |
| 4162W94 | | y | GlaxoWellcome | CD4 | | |
| 42/6 | mu | | Arizona Cancer Ctr. | transferrin receptor | | |
| 45-9 | | | Invitron | diagnostic | | |
| 4B5 | | | Novopharm | idiotype, melanoma, sclc | | |
| 4G8 | | | Senetek | Alzheimer's diagnostic | | |
| 5A4 | | | Invitron | diagnostic | | |
| 5A8 | | y | Biogen | CD45 | | |
| 5C8 | | y | Biogen/Antova | CD154 | | |
| 5G6.4 | | | Univ. of Michigan Med. Center | cancer | | |
| 64G12 | | | Pharma Pacific Australia | transplant rejection, other | | |
| 791T/36-RTA | | | Xoma | cancer | | |
| 81C6 | | | Duke University Medical Center | cancer | | |
| 85RC1 | | | Temple Univ. | prekallikrein/kallikrein | | |
| 87RP1 | | | Temple Univ. | Factors, X!!, X!!a, X!!f | | |

TABLE 1-continued

| Name | Origin | H | Source | Target | Acc/# | Note |
|---|---|---|---|---|---|---|
| 90-yttrium antiferritin | | | Hybritech | cancer | | |
| 93KA9 | hu | | Novartis | V.zoster glycoprotein II | | |
| A1-245 | | | Meiji Milk | cancer | | |
| A5B7-cisplatin conjugate | | | Glaxo Wellcome | cancer, other | | |
| AB19-4 | | | Tanox | anti idiotypic, HIV | | |
| Abciximab | mu/hu | | Centocor | cardiovascular disease | | |
| ABX-CBL | hu | | Abgenix | transplant rejection | | |
| ABX-EGF | hu | | Abgenix | EGFR | | Xenomous derived |
| ABX-IL8 | hu | | Abgenix | IL-8 | | Xenomous derived |
| ABX-LSN | | y | Abgenix | LAM-1 | | |
| ABX-RB2 | hu | | Abgenix | CBL antigen | | Xenomous derived |
| AD-439 | hu/mu | | Tanox | HIV | | |
| AD-519 | hu/mu | | Tanox | HIV | | |
| AIDS | | | Nissin Food Products | HIV | | |
| AIDS | | | Genelabs | HIV | | |
| AIDS | | | Becton Dickinson | HIV | | |
| AIDS | | | Kaketsuken | HIV | | |
| AIDS | hu | | Nissin Food Products | HIV | | |
| AIDS | | | Kaketsuken | HIV | | |
| AIDS (3H8) | | | Centocor | HIV | | |
| ALG-991 | | y | Allergene | poison ivy/poison oak | | |
| AML-2-23 | | | Medarex | CD14/CD15 | | |
| ANA vaccine | | | Procyon Biopharma | cancer, other | | |
| anti-alpha-TGF | | | NIH | cancer | | |
| Anti-Apo-1 | | | GermanCaRsrchCtr. | B cell tumor | | |
| anti-B cell tumor | hu | | U-BiSys | B-cell tumors | | |
| Antibacterial | | | Hybritech | gram negative bacteria | | |
| anti-bombesin | | | Hybritech | cancer | | |
| Anticancer | | | Hybritech | cancer, imaging agent, other | | |
| anticancer conjugates | | | NeoRx | cancer | | |
| anticancer vaccine | | | Immpheron | cancer, other | | |
| anti-CCR2 | | | LeukoSite | arthritis, atherosclerosis, multiple sclerosis | | |
| anti-CD11a | mu | | SangStat | transplant rejection | | |
| anti-CD14 scFv | | | U-BiSys | cancer, other | | |
| anti-CD18a | mu | | SangStat | transplant rejection | | |
| anti-CD19/CD3 scFv | | | Micromet | cancer | | |
| Anti-CD3H | ra | y | Oxford Univ./BTG UK | hum. CD3 Ag. | | |
| anti-class II | | | Univ. de Lille II | diabetes | | |
| anti-CTFG | hu | | FibroGen | fibrosis, other | | |
| anti-CTLA-4 | hu | | Medarex | cancer, infection, other | | |
| anti-EGF | | | Hybritech | cancer | | |
| antifibrin(+tPA) | | | Massachusetts Gen. Hospital | thrombosis | | |
| Antifibrotic | hu | | FibroGen | kidney fibrosis, transplant rejection, scleroderma, etc. | | |
| Antiganglioside | | | Nissin Food Products | cancer, diagnostic | | |
| anti-GM-CSF | | | AMRAD Corp. | arthritis | | |
| anti-HER2neu scFv | | | Micromet | cancer | | |
| anti-herpes | hu | | EPlcyte Pharmaceutical | Herpes virus, infection, other | | |
| anti-HFLA-1 | mu | | SangStat | transplant rejection | | |
| anti-HIV | hu | | BMS | gp120, pg41 | | |
| anti-HIV | hu | | NYU Medical Center | HIV, infection | | |
| anti-HSV-I | | | Glaxo Wellcome | Herpes simplex I | | |
| anti-idiotypic | | | Alliance Pharmeteutical | AIDS vaccine | | |
| anti-idiotypic | hu | | Karolinska Institute | cancer vaccine | | |
| anti-idiotypic | | | Texas Biotechnology | vaccine | | |
| anti-IFG-1 | | | Glaxo Wellcome | cancer, other | | |
| anti-IL-12 | | | Medarex | | | |
| anti-IL-15 | hu | | Medarex | inflammation, other | | |
| anti-IL-2R | | | American Home Products | arthritis | | |
| anti-IL-6 | | | Centocor | colitis, asthma, psoriasis, bone regeneration, osteoporosis, arthritis | | |
| anti-IL-8 | hu | | Medarex | | | |
| anti-LFA1 | mu | | SangStat | transplant rejection | | |
| Antilymphoma | | | Invitron | cancer | | |
| Antimelanoma | | | Institute of Medical and Veterinary Science, Adelaide | cancer | | |
| anti-MHC II | hu | | Genome Pharmaceuticals | multiple sclerosis, cancer | | |
| anti-myeloma scFv | | | Micromet | cancer | | |
| anti-pan-B | | | IDEC | cancer, other | | |
| anti-PCP | | | Univ. of Arkansas Med. Sciences | drug addiction, other | | |
| anti-RSV | mu | | NIH | respiratory syncytial virus, infection | | |
| anti-sperm | | | EPlcyte Pharmaceutical | contraceptive | | |

TABLE 1-continued

| Name | Origin | H | Source | Target | Acc/# | Note |
|---|---|---|---|---|---|---|
| anti-T4 | mu | | Univ. of Basel | arthritis | | |
| anti-Tac-PE40 | | | NIH | cancer | | |
| Antithrombosis | | | Teijin | alpha 2 plasmin inhibitors | | |
| anti-TNF | mu | | Genetech | GvHD | | |
| anti-TNF | | | Chiron | septic shock | | |
| Anti-TNF Mab | mu | | Celltech Ch. | TNF | | |
| anti-uPAR | | | Wilex Biotechnology | cancer, other | | |
| AuA1 | | | Imperial Cancer Research Fund | cancer | | |
| B1 | mu | | Coulter/SmithKline Beecham | CD20 | | |
| B4 | | | United Biomedical | CD4/HIV complex | | |
| B43 | | | University of Minnesota | CD19 | | |
| B72-3 | | | Celltech Chiroscience | cancer, diagnostic | | |
| B96-doxorubicin | | | Seattle Genetics | cancer, other | | |
| Basiliximab | | | Novartis | IL-2R | | bispecific |
| BAT-123 | | | Baylor College of Medicine | HIV | | |
| BBC-353 | | | Hybritech | cancer | | |
| BC-1 | | | Antisoma | oncofetal fibronectin | | |
| BD-95225 | | | Sanofi-Synthelabo | cancer | | |
| BD-95325 | | | Sanofi-Synthelabo | cancer | | |
| BIBH-1 | | | Boehringer Ingelheim | cancer | | |
| bispecific enzyme-drug coActive | | | Immunomedics | cancer, other | | |
| BIWA-4 | | | Boehringer Ingelheim | CD44v6 | | |
| BM12 | hu | | Merck | gp120 | | |
| BMS-181170 | hu | | BMS | group B strep. | | |
| boron-conjugates | | | Immunomedics | cancer, diagnostic | | |
| Bp-39 | mu | | Bristol-Myers-Squibb | cancer | | |
| BR96 | | | Seattle Genetics | pancarcinoma | | single chain ab. |
| BrevaRex | | | AltaRex | Idiotype, MUC-1 expressing tumors | | |
| BST-1004 | | | BioStratum | gamma2 laminin | | |
| BT-072 | | | Biotest | HbB surface antigen | | 1+ |
| BT563 | | | Biotest | IL-2R | | |
| BT-571 | | | Biotest | Rh(D) antigen | | 1+ |
| BTI-322 | mu | | BioTransplant | CD2 | | proprietary |
| BTI-322 | | | MedImmune/BioTransplant | CD2 | | |
| C11C1 | | | Temple Univ. | plasma kininogen | | |
| C215Fab | | | Pharmacia/Upjohn | tumor specific | | Fab |
| C225 | | | ImClone | EGFR | | |
| C46 | | | Nycomed Pharma/Cytogen | CEA | | |
| C5a neutralizing | | | Chiron | adult respiratory distress syndrome, septic shock | | |
| CA15-3 | | | Centocor | cancer | | |
| Capiscint | | | Centocor | imaging agent | | |
| Capromab pendetide | | | Cytogen | prostatic Ca. | | |
| CAT-152 | | | Cambridge Antibody Technology | TGFbeta2 | | |
| CAT-192 | | | Cambridge Antibody Technology | TGFbeta1 | | |
| catalytic | | | Igen | cancer, septic shock | | |
| CCR-5 | sh | | KS Biomedix | HIV | | |
| CDP-571 | | y | Celltech Chirosciences | TNF alpha | | |
| CDP-671 | | y | Celltech Chirosciences | PEM, polymorphic epithelium mucin | | |
| CDP-833 | | y | Celltech Chirosciences | colorectal tumors | | |
| CDP-835 | | y | Schering Plough | IL-5 | | |
| CDP-855 | | y | Celltech Chirosciences | MHC Class II | | |
| CDP-860 | hu | | Celltech Chirosciences | PDGF-R | | |
| CDP-870 | | | Celltech Chirosciences | anti inflammatory | | |
| CeaVac | mu | | Trilex | idiotype | | |
| CenC-18 | | | Centocor | neutrophil | | |
| Centara | | y | Centocor | CD45 | | |
| CGP-62360 | | | Novartis | idiotype, melanoma | | |
| ch14.18-IL-2 | hu/mu | | Merck KGaA | cancer, gene therapy | | |
| chimeric | hu/mu | | Teijin | cancer | | |
| chimeric | | | Abbott | cancer | | |
| ChL-6 | hum | | BMS | br; co; ov; lu CA | | |
| chTNT-3/B | | | Techniclone | cancer, other | | |
| Clenoliximab | mu | p | IDEC | CD4 | | |
| CMA-676 | | y | Celltech Chirosciences | CD33 | | |
| COL-1 | | | NIH | colon Ca. | | |
| Colostat-G | | | GalaGen | | | |
| Corsevin M | mu/hu | | Corvas | Factor VIIa | | |
| CTLA4Ig | | | BMS | B7 | | |
| CXCR-4 | sh | | KS Biomedix | HIV | | |
| CY-1747 | | | Epimmune | P-selectin | | |
| CY-1748 | | y | Epimmune | P-selectin | | |
| CY-1787 | | | Epimmune | ELAM | | |
| CY-1788 | | y | Epimmune | ELAM | | |
| Cyotsyn | | | CytoDyn | AIDS | | |
| CYT-103-Y90 | | | Cytogen | cancer | | |

TABLE 1-continued

| Name | Origin | H | Source | Target | Acc/# | Note |
| --- | --- | --- | --- | --- | --- | --- |
| Cytogen/Farmatalia | | | Cytogen | cancer | | |
| Cytolin | | | CytoDyn | AIDS | | |
| cytolytic | | | Univ. of Texas | trichomonas vaginalis antigen | | |
| Cytovir | | | Centocor | cytomegalovirus | | |
| D2E7 | | y | Cambridge Antibody Technology | TNF | | |
| dacliximab | | y | PDL | Tac/IL-2R | | |
| DD3B6/22 | | | Agen Biomedical | thrombosis, imaging agent | | |
| EC-708 | | | Biovation | colorectal Ca. | | |
| EMD-55900 | mu(my. 425 | | Merck | EGF-R | | |
| EMD-56700 | | | ImmunoGen | cancer | | |
| EMD-72000 | | y | Merck | EGF-R | | |
| endotoxin | | | American Home Products | bacterial toxins | | |
| endotoxin | | | Chiron | gram negative endotoxins | | |
| Enlimomab | mu | | Boehringer Ingelheim | ICAM-1 | | |
| ERIC-1 | | | ICRT | glioma, neural cell adhesion molecules | | |
| F105 | | | Centocor | | | |
| FC-2.15 | mu | | Fundacion Campomar | breast Ca. | | |
| FC-3001(+111-In) | | | Orion Pharma | imaging agent | | |
| FCE-27277 | mu | | Farmitalia Carlo Erba | TNF | | |
| Felvizumab | | y | Scotgen | RSV | | SB-209763 |
| fibrin | | | Centocor | immunoconjugation | | |
| FK-001/FK-5A5 | hu | | Sumitomo | psuedomonas aeruginosa exotoxin A | | |
| FU1-74 | | | Takeda | fibrin/urokinase | | bispecific |
| G-250 | | | Centocor | cancer | | |
| G3.519 | | | Tanox | HIV | | |
| G5-sFv | | | Monsanto | desipramine | | sFv fragment |
| Gama-interferon Mab | | | Centocor | gamma interferon | | |
| GI103 | | | Cytogen | gastrointestinal Ca. | | |
| GivaRex | | | AltaRex | Idiotype, CA19.9 expressing tumors | | |
| Gliomab-H | | | Novopharm | brain tumors | | |
| glycoside GD2 | | | Meiji Milk | cancer | | |
| GNI-250 | | | Sloan-Kettering | tumors | | |
| Gonorrhoea vac. (SMZ4) | | | Univ. of Southhampton Med. School | gonorrhoea | | |
| GT-4086 | | | Gliatech | inflammation, other | | |
| GW-353430 | | | GlaxoWellcome | CD23 | | |
| H17E2 | | | Imperial Cancer Research Fund | cancer | | |
| H57-597 | | | Hoechst Marion Roussel | GvHD | | |
| H65-TRA | mu | | Xoma | GvHD, diabetes, psoriasis, cancer | | |
| HA-1A | hu | | Centocor | gram negative infections, endotoxic shock | | |
| HCV-AB | hu | | XTL Biopharmaceuticals | hepatitis-C virus, infection | | |
| HD69 | | | Micromet | | | |
| HD69 | Micromet | hu | Micromet | cancer, other | | |
| hepatitis-B | hu | | Hybritech | hepatitis-B | | |
| Hepatitis-B | | | Southwest Foundation for Biomedical Res. | hepatitis-B virus | | |
| HMFG1 | | | VA Med Ctr. | milk fat globule | | |
| HMFG1 | mu | | Cancer Therapeutics/Antisoma | polymorphic epithelial mucin PEM-10 | | |
| HMFG-1 | | y | Antisoma/ICRT | epithelial tumors | | |
| HMFG-1 | | | Antisoma | cancer, other | | |
| HMGF1 | | | Imperial Cancer Research Fund | cancer | | |
| HMGF2 | | | Imperial Cancer Research Fund | cancer | | |
| hMN-4 | mu | y | Immunomedics | colorectal, breast Ca. | | |
| HNK-20 | | | OraVax | RSV | | |
| hPM-1 | | y | Chugai | IL-6R | | |
| HRV14 | | | Novartis | human rhinovirus type 14 | | |
| hu1124 | | y | Genentech/Xoma | CD11a | | |
| Hu1D10 | | y | PDL | HLA-DR | | |
| Hu23F2G | | y | ICOS | leukointegrin | | |
| Hu-901 | | | Tanox | allergy, other | | |
| HuABL-364 | mu | y | PDL | lewis Y antigen | | |
| huAnti-B4 | mu | y | ImmunoGen | B cell lymphomas | | |
| huC242 | | y | ImmunoGen | mucin-type glycoprotein ag. | | |
| HuDREG-200 | mu | y | PDL | LI-selectin | | |
| HuEP5C7 | | y | PDL | P and E selectins | | |
| HuHCMV16-2 | | y | Scotgen | CMV gpUL75 | | |
| HuM195 | mu | y | PDL | myeloid leukemia | | |
| HuM291 | | y | PDL | CD3 | | |
| HumaLYM | | | Intracel | cancer | | |
| HumaRAD | | | Intracel | cancer | | |

TABLE 1-continued

| Name | Origin | H | Source | Target | Acc/# | Note |
|---|---|---|---|---|---|---|
| HumaRESP | hu | | Intracel | respiratory syncytial virus, infection | | |
| HumaSpect | | | Intracel | cancer, diagnostic | | |
| HumaT4 | hu | | Intracel | transplant rejection, arthritis, allergies, other | | |
| huN901 | | y | ImmunoGen | sclc | | |
| HYB-241 | | | Hybritech | p-glycoprotein | | |
| hybrid tPA | | | Celltech Chiroscience | plasminogin activator stimulant, fibrino antagonist | | |
| IA-29 | | | Pharmacia Upjohn | ICAM | | |
| IC-14 | | | ICOS | septic shock | | |
| ICM3 | | y | ICOS | ICAM-3 | | |
| ICR-12 | | | ICRT/Taisho | c-erbB2 | | |
| IDEC-131 | | y | IDEC | gp39 | | |
| IgG1b12 | hu | | Scripps | HIV | | |
| IL-1 | | | Genzyme | IL-1 antagonist | | |
| IL-2 | | | Interferon Sciences | IL-2 receptor antagonist | | |
| IMG-BR-C | | | ImmunoGen | cancer | | |
| IMMU-LL2 | mu/hu | y | Immunomedics | B cell lymphomas | | |
| immunosuppressants | | | Celltech Chiroscience | transplant rejection, diabetes, arthritis, etc. | | |
| immunotargeted vaccine | | | Dartmouth College | infection | | |
| ImmunoTher | | | Endorex | cancer, diagnostic | | |
| Infliximab | ch | | Centocor | TNF alpha | | |
| Ior-c5 | mu | | Center of Molecular Immunology | o-linked glycoprotein | | |
| Ior-cea1 | mu | | Center of Molecular Immunology | cell-bound CEA | | |
| Ior-egf/r3 | mu | | Center of Molecular Immunology | EGFR | | |
| Ior-P3 | mu | | Center of Molecular Immunology | N-glycosylated gangliosides | | |
| Ior-T1 | mu | | Center of Molecular Immunology | hu CD6 | | |
| Ior-t3 | mu | | Center of Molecular Immunology | CD3 | | |
| J-695 | | y | Cambridge Antibody Technology | IL-12 | | |
| Junin vaccine | | | USAMRIID | Junin virus vaccine | | |
| K-18 | hu | | Kureha Chemical | cancer, other | | |
| Keliximab | | p | IDEC | CD4 | | |
| KS1/4-methotrexate | | | Hybritech | cancer | | |
| KS1/4-vinblastine | | | Eli Lilly | cancer, other | | |
| Kyowa Medex | | | Kyowa Hakko | cancer | | |
| L-6 | mu | | Bristol-Myers-Squibb | cancer | | |
| LDL haemoperfusion | | | Invitron | hypolipaemic/antiatherosclerosis | | |
| LDP-01 | | | LeukoSite | beta2 | | |
| LDP-02 | | y | LeukoSite | beta7 integrin | | |
| leptin | | | Cambridge Antibody Technology | obesity, diabetes, other | | |
| LeuTech | | | Palatin Technologies | diagnostic, infection | | |
| lipopolysaccharide | | | Celltech Chiroscience | septic shock | | |
| LL2 | | y | Immunomedics | CD22 | | Bectumomab |
| LM-609 | mu | | Isxys/Scripps | avb3 integrin | | |
| LM-CD45 | mu | | Cantab/Baxter | CD45 | | |
| LM-IBD1 | | | Cantab | | | |
| LS2D617 | mu | | Hybritech | cancer, imaging agent | | |
| LY-6 | | | Genetech | cancer | | |
| LYM-1 | mu | | Techniclone | cancer | | |
| M1 Mab | | | Accorda | remyelinating | | |
| M6b2 | | | Xijing Hospital | gastric Ca. | | |
| MA-16N7C2 | mu | | Corvas | human platelet GPIIb/IIIa | | |
| MaAb 5324 | hu | | Novartis | tetanus toxin | | |
| Mab 170 | | | Biomira | breast Ca. | | /technetium-99 |
| Mab 174 | | | Biomira | head and neck Ca. | | /technetium-99 |
| Mab 206 | mu | y | Scotgen | Varicella zoster | | |
| MAB 31.1 | | | Purdue Pharma | colon Ca. | | |
| Mab 60.1 | | | RepliGen | Mac-1 integrin, CD11b | | |
| Mab B3 | | | NIH | B3 antigen | | |
| Mab B42.13 | | | Biomira | ovarian Ca. | | |
| Mab B43.13 | mu | | Biomira/AltaRex | CA125 tumor associated ag. | | /technetium-99 |
| MAb + porphyrins | | | QTL PhotoTherapeutics | cancer, arthritis | | |
| MAb1 + MAb2 | | | Micromet | cancer | | |
| mAb-24 | | | Innogenetics/Chiron | B7 | | |
| MAK-195F | mu | | Knoll | TNF | | Fab |
| M-DC8 | | | Micromet | cancer, infection | | |
| MDX-11 | mu | | Medarex | myeloid leukemia, small cell lung Ca. | | |
| MDX-210 | | | Medarex | Her-2/neu | | |
| MDX-22 | | | Medarex | acute myeloid leukemia | | |
| MDX-220 | | | Medarex | glycoprotein TAG-72/H22 | | |
| MDX-240 | | | Medarex | gp41 | | |

TABLE 1-continued

| Name | Origin | H | Source | Target | Acc/# | Note |
|---|---|---|---|---|---|---|
| MDX-260 | | | Medarex | melanoma, neuroblastoma, glioma | | |
| MDX-33 | | y | Medarex | Fc receptor | | |
| MDX-447 | | y | Medarex/Merck | EGF-R/FcgammaR1 | | |
| MDX-CD4 | hu | | Medarex | arthritis | | |
| MEDI-488 | | | MedImmune | alphaV3 HIV-1 | | |
| Melimmune | | | IDEC | melanoma | | |
| Melo-Derm | | | Selective Genetics | malignant melanocytes | | |
| methotrexate | | | CRC Technology | cancer | | |
| MH-1 | | | Am. Biogenetic Sciences | cancer, thrombosis, imaging agent | | |
| Migis | | | Tanox | B cells, migis ags. | | |
| MKC-454 | | y | Mitsubishi Chemical | c-erbB-2 | | |
| MMA-383 | | | Novartis | idiotype, Lewis Y ag. | | |
| Monopharm-C | | | Novopharm | adenocarcinomas | | |
| MR6 | | | IC Innovations | IL-4R | | |
| MRA | | y | Chugai | IL-6R | | |
| MRK-16 | | | Ixsys/Hoechst Japan | p-glycoprotein | | |
| MRK17 | | | Ixsys/Hoechst Japan | p-glycoprotein | | |
| MS-705 | hum | | Mitsui | P. auruginosa | 1+ | |
| muromonab | mu | | Johnson & Johnson | transplant rejection, other | | |
| natalizumab | | y | Elan | VLA-4 | | |
| NG-1 | hu | | Hygeia/Novopharm | Neuroblastoma | | |
| NM-01 | mu | | Scotgen/Nissin | HIV | | |
| NOVOMAb-G2 | hu | | Novopharm | pancarcinoma | | scFv |
| NR-CO-02 | | | NeoRx | CEA expressing tumors | | /rhenium |
| NR-LU-10 | | | NeoRx | cancer | | |
| NR-LU-10-PE | | | NeoRx | breast Ca. | | /Pseudomonas exotoxin |
| NR-LU-13 | | | NeoRx | pancarcinoma tumors | | /rhenium |
| NR-ML-05 | | | NeoRx | hu. Melanoma-ass.proteoglycan | | |
| NR-ML-05 (+technetium-99m) | | | NeoRx | cancer detection | | |
| NT1 | | | Univ. de Lille II | adenovirus | | |
| OC-TR | | | Centocor | CD3/Mov18 | | bispecific |
| OKT-1 | | | Johnson & Johnson | cancer, other | | |
| OKT-10 | | | Johnson & Johnson | cancer, other | | |
| OKT-11 | | | Johnson & Johnson | cancer, other | | |
| OKT-4 | | | Ortho | T-cells | | |
| OKT-5 | | | Johnson & Johnson | cancer, other | | |
| OKT-6 | | | Johnson & Johnson | cancer, other | | |
| OKT-8 | | | Johnson & Johnson | cancer, other | | |
| Oncolysin B | | | Immunogen | cancer | | |
| ONCOLYSIN M | | | ImmunoGen | cancer | | |
| OVB-3 | | | NeoRx | | | PE toxin |
| OX-19 | | | Takeda | allograft rejection | | |
| P145 | | | Biosciences Corp. | cancer, diagnostic | | |
| P256 | | | Nycomed Pharma | platelets | | |
| PAB-240 | | | ICRT | p53 mutant | | |
| Palivizumab | | y | MedImmune | RSV fusion protein | | |
| PAM4 | mu | y | Merck | pacreatic Ca. | | |
| parathyroid-imaging | | | Washington Univ. School of Medicine | imaging agent | | |
| Pharmaproject No. 1891 | | | Univ. of Utah | oncogene protein p53 | | |
| Pharmaproject No. 1955 | | | Cytogen | cancer, GvHD | | |
| pharmaprojects no. 1979 | | | Institut Pasteur | HIV | | |
| Pharmaprojects No. 2026 | hu | | Mitsubishi Chemical | cancer | | |
| pharmaprojects no. 551 | | | Hoechst Marion Roussel | contraceptive | | |
| pharmaprojects no. 5856 | | | Cambridge Antibody Technology | therapeutics/diagnostics | | |
| pharmaprojects no. 5861 | hu | | Immunomedics | cancer, other | | |
| pharmaprojects no. 5868 | | | Immunomedics | restenosis, atherosclerosis | | |
| pharmaprojects no. 5876 | hu | | Abgenix | | | |
| pharmaprojects no. 5908 | | | Seattle Genetics | cancer | | |
| pharmaprojects no. 5909 | | | Seattle Genetics | cancer, other | | |
| pharmaprojects no. 5930 | hu | | Abgenix | | | |
| pharmaprojects no. 5953 | | | Medarex | infection, other | | |
| pharmaprojects no. 5990 | | | Medarex | | | |
| pharmaprojects no. 6024 | hu | | Millennium | inflammation, other | | |
| pharmaprojects no. 6063 | | | Active Biotech | septic shock | | |
| pharmaprojects no. 6066 | hu | | LeukoSite | inflammation, other | | |
| pharmaprojects no. 6131 | hu | | Abgenix | inflammation, other | | |
| pharmaprojects no. 6132 | | | Biovation | cancer | | |
| pharmaprojects no. 6168 | | | Abgenix | transplant rejection, other | | |
| pharmaprojects no. 6174 | hu | | Abgenix | cardiovascular disease | | |
| pharmaprojects no. 6175 | hu | | Abgenix | cancer, other | | |
| pharmaprojects no. 6200 | | | NIH | infection, respiratory tract | | |
| pharmaprojects no. 6212 | | | AMRAD Corp. | asthma | | |
| pharmaprojects no. 6228 | | | Inhibitex | infection | | |

TABLE 1-continued

| Name | Origin | H | Source | Target | Acc/# | Note |
|---|---|---|---|---|---|---|
| pharmaprojects no. 6256 | hu | | Abgenix | | | |
| pharmaprojects no. 6288 | | | Cytogen | cancer | | |
| pharmaprojects no. 6296 | | | Protein Design Labs | inflammation, other | | |
| pharmaprojects no. 6302 | | | Tanox | inflammation, infection, other | | |
| pharmaprojects no. 6314 | | | Corixa | cancer, infection, other | | |
| PNU-214565 | | | Pharmacia & Upjohn | cancer | | |
| PR1A3 | mu | y | Antisoma/ICRT | CEA | | |
| progesterone | | | Johnson & Johnson | progesterone antagonist | | |
| project no. D-0257 | hu | | Yissum | cancer, arthritis | | |
| prostate-specific | | | Corixa | cancer | | |
| PSA | mu | | AltaRex | cancer | | |
| pseudomonas | | | Teijin | pseudomonas infections | | |
| PSMA | | | Biovation | cancer | | |
| PylorImune-G | | | GalaGen | Helicobacter pylori | | |
| QUADROMA therapeutics | | | Quest Biotechnology | anticancer | | |
| R3 | | | Center for Molecular Immunology | cancer, imaging agent | | |
| ranpirnase | | | Alfacell | cancer, other | | |
| RDC | | | Research Development Corp. | arteriosclerosis | | |
| REGA-3G12 | mu | | Rega Institute | human neutrophil gelatinase | | |
| RFB4 | | | ICRT | CD22 | | |
| RG-83852 | | | Rhone-Poulenc Rorer | cancer | | |
| rhuMab-E25 | | y | Novartis/Tanox | IgE | | |
| RNase-conjugate | | | Immunomedics | cancer, other | | |
| rubella | | | Research Corp. Technologie | rubella virus | | |
| SB-240563 | | y | SmithKline Beecham | IL-5 | | |
| SB-240683 | | | SmithKline Beecham | asthma | | |
| SB-249417 | | y | SmithKline Beecham | Factor IX | | |
| SDZ-ABL-364 | mu | | PDL | lewis Y antigen | | |
| SDZ-CHH-380 | mu/hum | | Novartis | CD7 | | |
| SDZ-HSV-863 | hum | | Novartis | Herpes simplex1/2 | | |
| Sevirumab | hum | | Novartis | hCMV | | |
| SF-25 | | | Harvard Med. School | colon Ca. | | |
| Shigellin-G | | | GalaGen | Shigella | | |
| SIgA/G | | | Planet Biotechnology | dental caries | | |
| SM3 | | | ICRT | cancer | | |
| SMA-6H9 | sh | | KS Biomedix | colon Ca. | | |
| Sporidin-G | | | GalaGen | Cryptosporidium parvum | | |
| SS(dsFv)-PE38 | | | NeoPharm | cancer | | |
| SV2-61gamma | mu | | Ajinomoto | c-erbB2 | | |
| T101 | | | Clin Midy | T65 | | |
| T101 | | | NIH | leukemia | | |
| T101 (+DOX, +MTX, or +RTA) | | | Hybritech | cancer | | |
| T10B9 | mu | | MedImmune | transplant rejection | | |
| T2G1s | mu | | Centocor | antifibrin | | Fab |
| T2G1s | hu/mu | | Centocor | imaging agent | | |
| T-88 | | | Chiron | gram negative bacteria | | |
| TAb-250 | mu | | Schering AG | cancer, diagnostic | | |
| TES-123 | | | Chugai | endothelial cell surface ags. | | |
| TheraMAbs | mu/hu | | Xoma | hu cancer cell line C3347 | | |
| Thrombolitic | | | Holtech Medical | PAI1 | | |
| TI-23 | | | Teijin | human cytomegalovirus | | |
| TI-57 | hu | | Teijin | Varicella zoster virus | | |
| TM19 | | | Avant | | | TCAR-based |
| TM27 | | | Avant | MS? | | TCAR-based |
| TM29 | | | Avant | | | TCAR-based |
| TM31 | | | Avant | | | TCAR-based |
| Trastuzumab | | y | Genentech | Her-2 | | |
| TriAB | mu | | Trilex | idiotype, ovarian Ca. | | |
| Triclonal | | | Medimorphics | CMV/HIV | | |
| TriGem | mu | | Trilex | idiotype, malignant melanoma, sclc | | |
| Tuvirumab | hum | | PDL | HbB | | |
| TXU-PAP | | | Wayne Hughes Institute | | | |
| UBS-54 | | | U-BiSys | cancer | | |
| UCHL1 | | | ICRT | CD45RO | | |
| UJ13A | | | ICRT | glioma, neural cell adhesion molecules | | |
| UP4-33 | mu | | Takeda | GMP-140/urokinase | | bispecific |
| vindesine conjugates | | | Eli Lilly | cancer, other | | |
| WT1-ricin | | | Imperial Cancer Research Fund | Leukemia | | |
| XomaScan-791 | | | Xoma | cancer, imaging agent | | |
| XOMEN-0E5 | mu | | Xoma | septic shock | | |
| Xomen-PS | mu | | Xoma | septic shock | | |
| XTL-001 | | | XTL Biopharmaceuticals | HbB | | 1+ |
| YM-337 | | y | Yamanouchi | human platelet GPIIb/IIIa | | Fab |

TABLE 1-continued

| Name | Origin | H | Source | Target | Acc/# | Note |
|---|---|---|---|---|---|---|
| ZD-0490 | | | AstraZeneca | colon CA | | /ricin |
| ZME-018 + alpha-IF | | | Hybritech | cancer | | |
| 10C8 | | | Igen | | | |
| 125I-CC49 | | | Neoprobe Corp. | surgical management of cancer | | |
| 12B | | | Igen | | | |
| 15D8 | | | Igen | | | |
| 18B | | | Igen | | | |
| 1A | | | Igen | | | |
| 1C3 | | | Igen | | | |
| 1D | | | Igen | | | |
| 1E | | | Igen | | | |
| 2A | | | Igen | | | |
| 2A1 | | | Igen | | | |
| 2A4 | | | Igen | | | |
| 2A6 | | | Igen | | | |
| 2B | | | Igen | | | |
| 2F12 | | | Igen | | | |
| 3622W94 | | | Glaxo Wellcome | cancer | | |
| 3A | | | Igen | | | |
| 3B | | | Igen | | | |
| 3D | | | Igen | | | |
| 4162W94 | | | Glaxo Wellcome | arthritis | | |
| 4C2 | | | Igen | | | |
| 4D | | | Igen | | | |
| 4E | | | Igen | | | |
| 4E6 | | | Igen | | | |
| 5E | | | Igen | | | |
| 5T | | | Igen | | | |
| 6B | | | Igen | | | |
| 8T | | | Igen | | | |
| 9T | | | Igen | | | |
| Abciximab | | | Centocor | cardiac ischemic complications | | |
| ABX-CBL | | | Abgenix Inc. | GvHD | | |
| ABX-EFG | | | Abgenix Inc. | cancer | | |
| ABX-IL8 | | | Abgenix Inc. | psoriasis | | |
| Antegren | | | Athena Neurosciences Inc. | multiple sclerosis | | |
| Antegren | | | Athena Neurosciences Inc. | multiple sclerosis | | |
| Antegren | | | Elan Corp. Plc. | inflammation | | |
| Anti-CD18 | | | Hoffman-La Roche | hemorrhagic shock | | |
| Anti-FLK-1/KDR | | | ImClone Systems Inc. | cancer | | |
| Anti-HSV | | | Protein Design Labs Inc. | herpes | | |
| anti-interleukin-5 | | | Schering-Plough Corp. | asthma | | |
| Antithrombin III | | | Rhone-Poulenc Rorer/Centeon | sepsis | | |
| Anti-VEGF | | | Genetech | cancer | | |
| Anti-VZV | | | Protein Design Labs Inc. | shingles | | |
| Antova | | | Biogen | idiopathic thrombocytopenic purpura; lupus | | |
| Arcitumomab | | | Immunomedics | breast cancer imaging | | |
| Arcitumomab | | | Immunomedics | cancer detection | | |
| ATM 027 | | | Avant Immunotherapeutics Inc. | multiple sclerosis | | |
| B4 | | | United Biomedical Inc. | HIV | | |
| Basiliximab | | | Novartis | transplant rejection | | |
| BAYX-1351 | | | Bayer Corp. | septic shock | | |
| BEC2 | | | ImClone Systems/Merck KGaA | cancer | | |
| BrevaRex | | | AltaRex Corp. | cancer | | |
| BTI-322 | | | MedImmune | transplant rejection, steroid resistant GvHD | | |
| C225 | | | ImClone Systems | cancer | | |
| Campath | | | Ilex Oncology Inc. | leukemia | | |
| CD40 | | | Biogen | inhibits factor VII antibody | | |
| Cefditeron | | | RTAP Holdings Inc. | infections | | |
| Ceprate SC | | | CellPro Inc. | stem-cell enrichment | | |
| Citicoline sodium | | | Interneuron Pharmaceutical Inc. | ischemic stroke | | |
| Clenoliximab | | | Idec/SmithKline Beecham | arthritis | | |
| Cotara | | | Techniclone | glioma | | |
| Cytogam | | | MedImmune | | | |
| Cytolin | | | CytoDyn Inc. | AIDS | | |
| Daclizumab | | | Hoffman-La Roche | transplant rejection | | |
| Edrecolomab | | | Centocor | cancer | | |
| Enbrel | | | Immunex Corp. | arthritis | | |
| G250 | | | Centocor | cancer | | |
| Graftskin | | | Organogenesis Inc. | surgical, diabetic ulcers, burns, pressure ulcers | | |
| GW353430 | | | Glaxo Wellcome | arthritis | | |

TABLE 1-continued

| Name | Origin | H | Source | Target | Acc/# | Note |
|---|---|---|---|---|---|---|
| HNK20 | | | OraVax Inc. | complications due to syncytial virus infection | | |
| Herceptin | | | Genetech | | | |
| ICM3 | | | Icos Corp. | psoriasis | | |
| IDEC-CE9.1/SB2210396 | | | Idec Pharmaceuticals Corp. | arthritis | | |
| IDEC-Y2B8 | | | Idec Pharmaceuticals Corp. | B-cell non-Hodgkin's lymphoma | | |
| Immunoglbulin gamma E | | | Genetech | asthma, allergic rhinitis | | |
| Infliximab | | | Centocor/Schering-Plough | Crohn's disease, arthiritis | | |
| Infliximab | | | Centocor | arthritis | | |
| Iodine 131 tositumomab | | | Coulter Pharmaceutical Inc. | cancer | | |
| LDP-01 | | | LeukoSite Inc. | stroke | | |
| LDP-02 | | | Genetech | inflammation | | |
| LDP-03 | | | LeukoSite Inc. | leukemia | | |
| LeuArrest | | | Icos Corp. | trama-induce hemorrhagic shock, multiple sclerosis, myocardial infarction, stroke | | |
| LMY-2 | | | Techniclone | cancer, leukemia | | |
| LymphoCide | | | Immunomedics | cancer | | |
| LymphoScan | | | Immunomedics | B-cell lymphoma detection | | |
| Mab conjugate | | | Immunex Corp. | leukemia | | |
| MAK 196F | | | Knoll Pharmceutical Co. | sepsis | | |
| MCA 14.2 | | | Igen | | | |
| MDX-11 | | | Medarex Inc. | leukemia | | |
| MDX-210 | | | Medarex Inc. | cancer | | |
| MDX-22 | | | Medarex Inc. | leukemia | | |
| MDX-220 | | | Medarex Inc. | cancer | | |
| MDX-240 | | | Medarex Inc. | AIDS | | |
| MDX-260 | | | Medarex Inc. | melanoma, glioma | | |
| MDX-33 | | | Medarex Inc. | idiopathic thrombocytopenic purpura | | |
| MDX-447 | | | Medarex Inc. | cancer | | |
| MDX-RA | | | Medarex Inc. | secondary cataracts | | |
| MEDI-500 | | | MedImmune | transplant rejection | | |
| MEDI-507 | | | MedImmune | transplant rejection, steroid resistant GvHD | | |
| MEDI-507 | | | MedImmune | psoriasis | | |
| Melacine | | | Ribi ImmunoChem Research Inc. | melanoma | | |
| MH-1 | | | American Biogenetic Sciences Inc. | angioplasty, dissolve blood clots | | |
| Odulimomab | | | Pasteur Merieux Connaught | transplant rejection, ischemia reperfusion injury | | |
| Oncolym | | | Techniclone | non-Hodgkin's B-cell lymphoma | | |
| Oncaspar | | | Enzon | | | |
| OrthocloneOKT3 | | | OrthoBiotech | HvGD | | |
| OvaRex | | | AltaRex Corp. | cancer | | |
| Palivizumab | | | MedImmune Inc./Abbott | syncytial virus diseases | | |
| Remicade | | | Centocor | Crohn's disease | | |
| Respigam | | | MedImmune | | | |
| Rituximab | | | Idec Pharmaceuticals Corp. | B-cell non-Hodgkin's lymphoma | | |
| SB 249417 | | | SmithKline | acute coronary syndrome | | |
| Synagis | | | MedImmune | | | |
| Smart ABL 364 | | | Protein Design Labs Inc. | cancer | | |
| Smart Anti-CD3 | | | Protein Design Labs Inc. | transplant rejection, autoimmune diseases | | |
| Smart Anti-E/P | | | Protein Design Labs Inc. | trauma, asthma, autoimmune diseases, stroke | | |
| Smart Anti-L | | | Protein Design Labs Inc. | reperfusion injury, trauma, stroke, respiratory distress syndrome | | |
| Smart M195 | | | Protein Design Labs Inc. | leukemia | | |
| Smart M195 (+bismuth 213) | | | Protein Design Labs Inc. | leukemia | | |
| Sulesmab | | | Immunomedics | osteomyelitis and acute atypical appendicitis detection | | |
| T10B9 | | | MedImmune Inc. | GvHD | | |
| TA-650 | | | Tanabe Seiyaku | arthritis | | |
| Theragyn | | | Antisoma Plc. | cancer | | |
| Theragyn | | | Antisoma Plc. | cancer | | |
| TTMA | | | Pharmacia & Upjohn Inc. | cancer | | |
| Votumumab | | | Intracel Corp. | cancer | | |

TABLE 1-continued

| Name | Origin | H | Source | Target | Acc/# | Note |
|---|---|---|---|---|---|---|
| Antithymocyte globulin | | | SangStat Medical Corp./Pasteur Merieux Connaught | transplant rejection | | |
| Candistat-G | | | GalaGen Inc. | thrush | | |
| Diffistat-G | | | GalaGen Inc. | antibiotic-associated diarrhea | | |
| Nabi-Altastaph | | | Nabi | infections | | |
| PylorImune-G | | | GalaGen Inc. | Helicobacter pylori infection-associated complications | | |
| B7 | | | Idec Pharmaceuticals Corp. | autoimmune diseases | | |
| Cancer cocktail | | | Centocor | cancer | | |
| CDP850 | | | Celltech Group Plc. | psoriasis | | |
| CDP860 | | | Celltech Group Plc. | restenosis | | |
| CMB401 | | | Celltech Group Plc. | cancer | | |
| CMI-392 | | | CytoMed. Inc. | psoriasis | | |
| CytoGam | | | MedImmune Inc. | cytomegalovirus disease | | |
| OST 577 | | | Protein Design Labs Inc. | hepatitis B | | |
| Primatized B7 | | | Idec Pharmaceuticals Corp. | inflammation | | |
| Primatized CD23 | | | Idec Pharmaceuticals Corp. | allergic rhinitis | | |
| SB 240563 | | | SmithKline | asthma | | |
| SB 240683 | | | SmithKline | asthma | | |
| Smart antigamma-interferon | | | Protein Design Labs Inc. | autoimmune diseases | | |
| Sporidin-G | | | GalaGen Inc. | diarrhea in immuno-compromised patients | | |
| Trastuzumab | | | Hoffmann-La Roche | cancer | | |
| Tru-Scint AD | | | Biomira Inc. | breast cancer | | |
| Tru-Scint AG | | | Biomira Inc. | breast cancer | | |
| HeFi-1 | Mu | | National Cancer Institute | CD30 | | |
| M44 | Mu | | National Cancer Institute | CD30 | | |
| KOLT-4 | | | Accurate Scientific | CD28 | | |
| Clone 37.51 Mab | Hamster | | Research Diagnostics | CD28 | | |
| CD28.2 | Mu | | Pharmingen | CD28 | | |

TABLE 2A

THERAPEUTIC ANTIBODIES ON THE MARKET

| Name | Company | Indication | Partner | How Developed? | Approval | 1998 Sales |
|---|---|---|---|---|---|---|
| REOPRO antibody | Centocor | Reduce acute blood clot related complications for high-risk angioplasty/coronary intervention patients | Lilly | | December 1994 | |
| ORTHO-CLONE OKT3 antibody | OrthoBiotech | Reversal of acute kidney transplant rejection | AHP, Baxter | | June 1986 | |
| RESPIGAM antibody | MedImmune | Prevention of respiratory synctytial virus in infants with bronchopulmonary dysplasia or history of prematurity | AHP/Baxter | | January 1996 | |
| RITUXAN antibody | Genentech | Non-Hodgkin's, low grad B-cell lymphoma | IDEC, Roche | | November 1997 | |
| ZENAPAX antibody | Hoffmann-LaRoche | Prevention of kidney transplant rejection | PDL | PDL humanization | December 1997 | |
| SIMULECT antibody | Novartis | Prevention of acute rejection episodes in kidney transplant recipients | Ligand | | May 1998 | |
| SYNAGIS antibody | MedImmune | Prevention of RSV in premature infants and bronchopulmonary disease | AHP, Abbott, Boehringer Ingelheim | | June 1998 | |
| REMICADE antibody | Centocor | Crohn's disease including those patients with fistula | Tanabe, Schering-Plough | | August 1998 | |

TABLE 2A-continued

THERAPEUTIC ANTIBODIES ON THE MARKET

| Name | Company | Indication | Partner | How Developed? | Approval | 1998 Sales |
|---|---|---|---|---|---|---|
| HERCEPTIN antibody | Genentech | Advanced metastatic breast cancer, where tumors overexpress the HER2 protein | Roche (outside U.S.) | | September 1998 | |
| CYTOGAM (CMV immune globulin IV) | MedImmune | Prevention of cytomegalovirus in kidney transplant patients for prophylaxis against CMV disease associated with kidney, lung, liver, pancreas and heart transplants. | None | | December 1998?? | |

TABLE 2B

THERAPEUTIC ANTIBODIES IN CLINICAL DEVELOPMENT

| Product | Indication | Company | Partner | Development Status | Comments |
|---|---|---|---|---|---|
| Mab to TNF (chimeric Remicade) | Rheumatoid arthritis | Centocor | Tanabe, Schering Plough | NDA filed January 1999 - Now in active review | Chimeric |
| CroTab polyclonal abs | Snake venom poisoning | Therapeutic Antibodies | Altana | NDA filed April 1998 - Now in active review | Polyclonal |
| Mab to IgE | Allergic rhinitis | Genentech | Novartis, Tanox | Phase III | Humanized |
| Mab to IgE | Allergic asthma | Genentech | Novartis, Tanox | Phase III | Humanized |
| Mab conjugated with Iodine 131 ("Bexxar") | Non-Hodgkin's lymphoma | Coulter | SmithKline Beecham | Phase III | |
| Mab to 17-1A ("Panorex") | Colorectal cancer | Centocor | Glaxo | Phase III | Murine |
| Mab to CA125 ("OvaRex") | Ovarian cancer, epithelial | AltaRex | None | Phase II/III | |
| Mab to CAMPATH | Chronic lymphocytic leukemia | Leukosite | Ilex Oncology | Phase III | Humanized |
| Mab to CD20 in combo with CHOP chemotherapy ("Rituxan") | Non-Hodgkin's | Genentech | IDEC, Roche, Zenyaku Kogyo | Phase III | |
| Mab to CD20 ("IDEC-Y2B8) | Targeted radiation therapy of non-Hodgkin's B-cell lymphoma | IDEC | None | Phase III | Chimeric |
| Mab to CD33 ("SMART M195") | Acute myeloid leukemia | PDL | Kanebo | Phase II/III | Humanized |
| Mab to CD33 linked to calicheamicin ("CMA 676" or "CDP 771") | Acute myeloid leukemia | CellTech | AHP | Phase II/III | |
| Mab to EGF receptor ("C225") | Head and neck cancer, squamous cell | ImClone | Merck | Phase III | Chimeric |
| Mab to idiotype BEC2 | Lung cancer, small cell | ImClone | Merck | Phase III | |
| Mab to LYM-1 ("HLA-DR10"), second-generation Oncolym | Non-Hodgkin's lymphoma | Techniclone | Schering | Phase II/III | |
| DigiTAb | Digoxin poisoning in congestive heart failure | Therapeutic Antibodies | Altana | Phase III | |
| Mab to platelet gpIIb/IIIa ("ReoPro") | Unstable angina | Centocor | None | Phase III | Chimeric |
| Mab to platelet gpIIb/IIIa ("ReoPro") | Adjuvant therapy with stents | Centocor | Lilly, Fujisawa | Phase III | Chimeric |
| Mab to respiratory syncytial virus, intranasal | Pneumonia bronchitis caused by RSV | Peptide Therapeutics (aka OraVax) | None | Phase III | |

TABLE 2B-continued

THERAPEUTIC ANTIBODIES IN CLINICAL DEVELOPMENT

| Product | Indication | Company | Partner | Development Status | Comments |
|---|---|---|---|---|---|
| Mab to leukointegrin ("Hu23F2G" or "LeukArrest") | Ischemic stroke | ICOS | None | Phase III | Humanized |
| Mab T10B9 ("MEDI-500") | Prevent graft vs host disease by ex vivo bone marrow depletion in leukemia and lymphoma patients | MedImmune | BioTransplant | Phase III | |
| Mab to LFA | Prevent delayed graft function | SangStat Medical | None | Phase III | |
| Mab Hu901 | Anaphylactic reaction to peanuts | Tanox Biosystems | None | Phase I | Chimeric Humanized |
| Mab to IL-5 ("DCP835" or "SCH55700") | Asthma, severe | CellTech | Schering-Plough | Phase I | |
| Mab to CD4 ("IDEC-151") | Rheumatoid arthritis | IDEC | SmithKline | Phase II | Primatized Second-generation |
| Mab to complement C5 ("5G1.1") | Rheumatoid arthritis | Alexion | None | Phase I/II | |
| Mab to TNF ("CDP571") | Crohn's disease, rheumatoid arthritis | CellTech | None | Phase II | Humanized |
| Mab to CD4 ("IDEC CE9.1") | Asthma | IDEC | SmithKline | Phase II | Primatized |
| Mab to CD3 ("SMART anti-CD3") | Transplant rejection and autoimmune diseases | PDL | None | Phase I/II | Humanized |
| Mab to CD4 ("MDX-CD4") | Autoimmune diseases | Medarex | Eisai | Phase I/II | Human |
| Mab to CD40 ligand ("Antova") | Immune thrombocytopenia purpura | Biogen | None | Phase II | |
| Mab to CD40 ligand ("Antova") | Lupus nephritis | Biogen | None | Phase II | |
| Mab to CD40 ligand ("IDEC-131") | Systemic lupus erythematosis | IDEC | Eisai | Phase II | |
| Mab to complement C5 ("5G1.1") | Lupus nephritis | Alexion | None | Phase I/II | |
| Mab ("MDX-33") | Immune thrombocytopenic purpura | Medarex | Centeon | Phase II | Biospecific |
| OncoRad | Prostate cancer | Cytogen | None | Phase II | |
| NOVOMab-G2 IgG | Non-Hodgkin's lymphoma | NovoPharm Biotech | None | Phase I | |
| NOVOMab IgM | Melanoma, malignant | NovoPharm Biotech | None | Phase I | |
| NovoMab-G2 scFv | Non-Hodgkin's B-cell lymphoma, recurrent | NovoPharm Biotech | None | Phase I | |
| Mab to CEA | Therapy of breast, colorectal, lung and ovarian cancers | Immunomedics | None | Phase I | Humanized Radiolabeled |
| Mab to CEA | Therapy of pancreatic cancer | Immunomedics | None | Phase I | Humanized Radiolabeled |
| Mab to EGF receptor (""C225") | Head and neck cancer, refractory | ImClone | Merck | Phase II | Chimeric |
| Mab to EGF receptor (""C225") | Pancreatic cancer | ImClone | Merck | Phase II | Chimeric |
| Mab to erbB-2 | Solid tumors | Chiron | PolyCell | Phase I | |
| NOVOVAC-M1 | Melanoma, malignant | NovoPharm Biotech | None | Phase I | |
| CEAVac | Lung cancer, non-small cell and colon cancer | Titan | None | Phase I/II | |
| CEAVac | Colorectal cancer | Titan | None | Phase II | |
| TriAB | Breast, lung, ovarian cancer | Titan | None | Phase 2 | |
| TriGem | Melanoma | Titan | None | Phase I/II | |
| Mab to ideotype BEC2 | Melanoma | ImClone | Merck | Phase II | |
| CDF-grafted LM 609 | Halt angiogenesis in solid tumors | Ixsys | MedImmune | Phase II | |
| LymphoCide | Therapy of non-Hodgkin's B-cell lymphoma | Immunomedics | None | Phase I | |

TABLE 2B-continued

THERAPEUTIC ANTIBODIES IN CLINICAL DEVELOPMENT

| Product | Indication | Company | Partner | Development Status | Comments |
|---|---|---|---|---|---|
| BrevaRex | Metastatic cancer, multiple myeloma | AltaRex | None | Phase I | |
| CMB 401 | Ovarian, lung cancer | CellTech | AHP | Phase II | |
| Mab to VEGF | Solid tumors | Genentech | None | Phase II | Humanized |
| MDX-11 | Acute myeloid leukemia | Medarex | None | Phase II | Bispecific |
| MDX-22 | Acute myeloid leukemia in bone marrow transplants | Medarex | None | Phase II | Bispecific |
| MDX-447 | Head and neck cancer, other EGF-R positive | Medarex | Merck | Phase II | |
| MCX-210 | Breast, colon, ovarian cancer; other HER-2 positive cancers | Medarex | Novartis | Phase II | |
| MDX-210 | Prostate cancer, metastatic | Medarex | Novartis | Phase II | |
| MCX-220 | Cancer, TAG-72 positive | Medarex | None | Phase I/II | |
| Mab, single chain | Cancer | Enzon | Seattle Genetics | Phase I | |
| Mab to CD18 | Acute myocardial infarction | Genentech | None | Phase II | Humanized |
| 5G1.1 SC | Cardiopulmonary bypass | Alexion | Procter & Gamble | Phase II | |
| 5G1.1-SC | Acute myocardial infarction | Alexion | Procter & Gamble | Phase I | |
| Hu23F2G; LeukArrest | Myocardial infarction | ICOS | None | Phase II | Humanized |
| Hu23F2G; LeukArrest | Hemorrhagic shock, trauma-induced | ICOS | None | Phase II | Humanized |
| ReoPro | Acute myocardial infarction | Centocor | Lilly/Fujisawa | Phase II | |
| IDEC-114 | Psoriasis | IDEC | Mitsubishi | Phase I | Primatized |
| MEDI-507 | Psoriasis | MedImmune | BioTransplant | Phase I | Humanized |
| CDP-850 | Psoriasis | CellTech | None | Phase I/II | Human |
| ABX-IL8 | Psoriasis | Abgenix | None | Phase I/II | Human |
| ICM3 | Psoriasis | ICOS | None | Phase I/II | Humanized |
| LDP-02 | Crohn's disease and ulcerative colitis | LeukoSite | Genentech | Phase I | Humanized |
| Norasept | Crohn's disease, rheumatoid arthritis | CellTech | None | Phase II | Humanized |
| Antova | Immune thrombocytopenia purpura | Biogen | None | Phase II | |
| Antova | Hemophilia A and Factor VIII inhibition | Biogen | None | Phase I | |
| OST 577 | Hepatitis B and liver transplantation | PDL | Novartis | Phase II | Humanized |
| Hu1124 | Psoriasis | Genentech | XOMA | Phase II | Humanized |
| Synagis; MEDI-493 | Respiratory syncytial virus in bone marrow transplants | MedImmune | None | Phase I/II | Humanized |
| CANDISTAT-G | Oral and esophageal candidiasis | GalaGen | None | Phase I/II | Polyclonal Oral |
| DIFFISTAT-G | Antibiotic-associated diarrhea | GalaGen | None | Phase II | Polyclonal |
| DiffGam | Diarrhea | ImmuCell | None | Phase II | Polyclonal Bovine |
| CryptoGAM | Prevent cryptosporidiosis | ImmuCell | None | Phase I/II | Polyclonal |
| Altastaph | Prevent staphylococcal infection in neonates | NABI | None | Phase II | Polyclonal |
| Antova | MS | Biogen | None | Phase I | |
| Antegren | MS | Elan (Athena) | None | Phase II | Humanized |
| LeukArrest | MS | ICOS | None | Phase II | Humanized |
| AnergiX | MS | Corixa | None | Phase I | Humanized |
| LDP-01 | Kidney transplantation and ischemic stroke | LeukoSite | None | Phase I/II | Humanized |

TABLE 2B-continued

THERAPEUTIC ANTIBODIES IN CLINICAL DEVELOPMENT

| Product | Indication | Company | Partner | Development Status | Comments |
|---|---|---|---|---|---|
| ReoPro | Stroke | Centocor | Lilly, Fujisawa | Phase II | Chimeric |
| IC14 | Sepsis | ICOS | None | Phase I | |
| ABX-CBL | Graft vs host | Abgenix | None | Phase II | Mouse |
| MEDI-507 | Graft vs host | MedImmune | BioTransplant | Phase II | Humanized |
| MEDI-507 | Transplantation induction | MedImmune | BioTransplant | Phase I/II | Humanized |
| Antova | Kidney transplantation | Biogen | None | Phase II | |
| Antova | Pancreatic transplantation | Biogen | None | Phase II | |
| Zenapax | Pediatric kidney transplantation | Biogen | None | Phase II | Humanized |
| R-24 | GD3 ganglioside, anticancer reagent | Memorial Sloan-Kettering | None | Phase I | Mouse |
| 2B2 | GD3 ganglioside | Genetic Systems | Bristol-Myers Squibb | | Mouse |
| IF4 | GD3 ganglioside | Genetic Systems | Bristol-Myers Squibb | | Mouse |
| MG-21 | GD3 ganglioside | Genetic Systems | Bristol-Myers Squibb | | Mouse |
| BW-494 | Adenocarcinoma | Behringwerke | Hoechst Marion Roussel | Phase I | |

One common recombination format, often referred to as "family shuffling" is practiced by recombining a selected nucleic acid with a homologous nucleic acid (i.e., for purposes of this disclosure, a nucleic acid with sufficient sequence similarity to permit physical recombination to occur between the nucleic acid at issue). Typically, homologous nucleic acids are at least about 50% identical, often 60% or more identical, generally 70% or more identical, and occasionally 80%, 90%, or even 95% or more identical. Such homologous nucleic acids can be components of a phage display library or can result from immunization of one or more animal with a given antigen. Alternatively, homologous nucleic acids can be members of gene families selected from the Immunoglobulin Superfamily, e.g., T cell receptor genes. Such nucleic acids provide a significant source of diversity in the antigen binding domain as well as contributing novel functional attributes.

Specific Selection Strategies.

As noted, any appropriate selection method in the art can be used to optimize antibody selection following diversification (e.g., by nucleic acid shuffling procedures). The following approaches provide examples of specific selection approaches.

(a) Selection for Increased Antigen-binding Affinity.

There are several different approaches for affinity selection. One method uses soluble antigen as a competitor in the selection reaction. If the concentration of competitor is near the KD of the parent clone, then clones with increased affinity will be preferentially bound to the fixed antigen. Another approach is to reduce the concentration of matrix-bound antigen to a level at or below the KD of the parent clone, thus creating a preferential selection for higher affinity mutants. To avoid masking of epitopes by random binding of antigen to a matrix, selection can be performed in solution (Hawkins et al. (1992) "Selection of phage antibodies by binding affinity. Mimicking affinity maturation" *J Mol Biol* 226: 889-96). In this case, Fab-phage bind to biotinylated antigen in solution which allows capture by streptavidin-coated magnetic beads. An entirely different approach allows unrestricted binding of phage to an antigen-bound matrix, and higher affinity clones are selected by elution under increasing stringent conditions (Schier and Marks (1996) "Efficient in vitro affinity maturation of phage antibodies using BIAcore guided selections" *Hum Antibodies Hybridomas* 7: 97-105). In an alternative approach, a yeast or bacterial display system is used and binding to a fluorescent antigen of interest is evaluated by flow cytometry. Progressively decreasing antigen concentrations into the picomolar range results in selection of clones with increasing affinity.

(b) Selection for Increased Antigen-binding Specificity.

Usually, affinity maturation is sufficient to produce an antibody that binds tightly to only one epitope on the desired antigen. Binding specificity can be monitored by ELISA assays against related antigens, by microscopic assays of labeled antibodies on whole cells, by competitive phage selection, (see, e.g., Dennis, M. et al., (1994) "Kunitz domain inhibitors of tissue factor-factor VIIa. II. Potent and specific inhibitors by competitive phage selection." *J Biol Chem.* September 2; 269(35):22137-44), or other soluble competition assays, (e.g. Cunningham, B. et al, (1994) "Production of an atrial natriuretic peptide variant that is specific for type A receptor." *EMBO J* Jun 1; 13(11):2508-15, orby specific in vivo effects.

(c) Selection for Decreased Immunogenicity.

Whenever mutagenesis is employed, there is a chance that the resulting molecule will be recognized as foreign by the human immune system. Repeated backcrossing of an evolved antibody with a human clone by DNA recursive sequence recombination (e.g., shuffling) can reduce immunogenicity (see also, Crameri et al. (1996) "Construction and evolution of antibody-phage libraries by DNA shuffling" *Nat Med* 2: 100-2).

Furthermore, non-human antibodies can be humanized by repeated recombination (e.g., shuffling) of coding nucleic acids with human antibody genes, e.g., with libraries of human antibodies.

Additionally, antibodies can be modified to eliminate human MHC class II binding peptides within the antibody, thus, reducing the ability of human T cells to recognize fragments of the antibody as foreign. In cases where elimination of class II binding peptides results in a reduction in affinity, the affinity of the antibody for antigen can be improved using, e.g., DNA shuffling or other diversity generating and selection procedures, as described herein.

(d) Selection for Increased Stability.

Stability of an antibody a variety of buffer conditions, as well as after repeated cycles of denaturation and renaturation is of significant utility in the commercial production and application of antibody reagents. Candidate antibodies can be evaluated for their antigen binding and other properties after exposure to, e.g., buffers of different ionic strength and pH, denaturing agents. Furthermore, activity can be evaluated after multiple cycles of denaturation and renaturation, as well as after purification by any of a number of methods. Such evaluations can include among other parameters, assessment of folding rate and efficiency. Other desirable attributes such as column binding on/off rates, column durability, low non-specific binding, and the like are also suitable for selection by the methods of the present invention.

(e) Selection for Modified Effector Function.

Screening or selection strategies can be designed to optimize effector function as well as antigen binding. In these cases, assays which evaluate the constant or Fc region are applied. Such assays include in vitro assays, e.g., complement fixation, complement mediated cell lysis, Fc receptor binding, as well as in vivo assays conducted in model systems, most frequently, the mouse. In vivo assays which measure stability via serum half-life, clearance of toxins or other small molecules, or resistance to a pathogenic challenge can be used to select antibodies with enhanced functions.

Antibody-ligand binding in solution is often inadequate for neutralization or therapeutic application. Thus while improvements gained in affinity and specificity can drastically enhance binding properties, these improvements do not necessarily result in an antibody which provides enhanced functional capabilities. For example, to effectively destroy a tumor cell, an antibody must first be able to bind an antigen on the tumor cell with high affinity and specificity. It must then be able to mediate destruction of the tumor cell bearing the antigen. One well known mechanism of antibody-linked cell destruction is the complement mediated lysis pathway. This lysis process is initiated by the fixation of the C1q complement component by an antibody constant region, or Fc.

In addition to binding complement components, the Fc domains of the different antibody isotypes are bound by a family of Fc receptors, which mediate such functional aspects as opsonization and phagocytosis, and activation of natural killer cells in antibody-dependent cell-mediated cytotoxicity (ADCC). Numerous assays, known in the art, are available to evaluate the capacity of variant (e.g., shuffled) antibody and Fc domains to perform in one or more of these processes.

Applications of Antibody Evolution

Evolution of Novel MAb Magic Bullets.

(a) Targeting antigens to antigen presenting cells (APCs). Antigen-MAb fusions can be a powerful means for targeting antigens to antigen presenting cells, such as dendritic cells (DCs). A rapid, specific and potent means of targeting antigens to professional APCs achieves a more rapid protective immune response, and a more robust immune response for a given dose of antigen, than is observed for standard immunizations. This effect is useful when rapid countermeasures are required, such as when the antigen-antibody fusion is used as a biological warfare counter agent or in an area of rapidly emerging disease, or where delivery of antigen is limiting as in DNA immunization or novel antigen delivery devices such as transdermal patches.

For example, the MAb N418 reacts specifically with an integrin present on murine DCs (Metlay et al. (1990) "The distinct leukocyte integrins of mouse spleen dendritic cells as identified with new hamster monoclonal antibodies" *J Exp Med* 171: 1753-71). The VH and VL sequences from N418 can be cloned into an antibody phage-display vector. Phage-Fab are produced and used to immunize mice. Immunization with phage-Fab is compared with wild-type phage and differences in the onset time of the anti-phage immune response could be monitored.

A human MAb that binds specifically to human DCs can then be produced. For example, large naïve human libraries are panned against human DCs, and specificity is monitored by cross-reaction to other human cell types. If additional diversity is desirable, then MAbs similar to the murine N418 could be generated, recombined and or mutated, e.g., shuffled, screened on human DCs, and then humanized for immunotherapy.

An alternative to MAb-antigen fusions for targeted immunization could employ MAb-phage-antigen fusions. By creating fusions between antigen and the phage proteins pVII or pIX (Gao et al., (1999) "Making artificial antibodies: a format for phage display of combinatorial heterodimeric arrays" *Proc Natl Acad Sci USA* 96: 6025-30), antigens can be displayed on the opposite end of the phage with respect to the gIII-fused FAbs. If the displayed FAb is specific to DCs, then the fused antigen can be effectively delivered. This process has the advantage that MAbs need not be subcloned into new vectors to create MAb-antigen fusions.

(b) Targeting of immunostimulatory sequences to APCs. Filamentous bacteriophage such as M13 carry a circular, single-stranded DNA (ssDNA) molecule encased by coat proteins. Targeting Fab-phage to APCs affords a novel method of delivering phage DNA to lymphocytes. Delivered DNA can serve an immunostimulatory function, e.g. as a vaccine or therapeutic agent, as a result of certain sequence motifs that it may contain. Portions of the phage genome could be replaced with known immunostimulatory sequences (ISS) or by sequences that have been optimized for ISS activity byrecombination or mutagenesis procedures, such as DNA shuffling. Typically, when oligonucleotides are used as ISS agents, they are prepared with phosphorothioate bonds to increase their in vivo stability. Phage can be grown in sodium thiophosphate to add phosphorothioate bonds to their DNA.

(c) Isolation and evolution of novel tumor-specific MAbs. Antibody phage-display has been successfully used to isolate tumor-specific Mabs (Kupsch et al., (1999) "Isolation of human tumor-specific antibodies by selection of an antibody phage library on melanoma cells" *Clin Cancer Res* 5: 925-31). The technology platform herein can be used to generate novel MAbs specific to any tumor type. MAbs can be evolved for increased binding affinity, specificity, and reduced antigenicity.

Evolution of Novel MAb Antagonists.

Antibodies are antagonists of non-host molecules. MAbs can be generated against neutralizing epitopes of infectious agents, optimized by DNA diversification and selection procedures (e.g., nucleic acid shuffling methods), and used for passive immunotherapy. MAbs are currently being evaluated for passive immunotherapy of HIV (Parren and Burton (1997) "Antibodies against HIV-1 from phage display libraries: mapping of an immune response and progress towards antiviral immunotherapy" *Chem Immunol* 65:18-56), HSV (Protein Design Labs, Inc.), Hepatitis B (Protein Design Labs, Inc.), and others.

Major efforts are underway to design MAbs that inhibit normal cellular functions for therapeutic benefit, such as blocking specific receptors or their ligands. In fact, the majority of all MAbs currently in development fall into this category. One example is anti-TNF-alpha therapy for rheumatoid arthritis. MAb therapies currently exist (Infliximab, Centocor, Inc.) but can be improved by optimizing MAbs by molecular evolution as described herein.

Evolution of Novel MAb Agonists.

Ligand-induced dimerization or oligomerization of receptors is a well-established mechanism of signal transduction (Castellino and Chao (1996) "Trans-signaling by cytokine and growth factor receptors" *Cytokine Growth Factor Rev* 7:297-302). Many clinically important receptors utilize this mechanism, including growth factor receptors, G protein-coupled receptors, cytokine receptors and trophic factor receptors. Because antibodies contain at least two identical antigen binding sites, Mabs can mimic the oligomer-inducing signal transduction abilities of the native ligand. Using phage display, MAbs are selected to bind to selected receptors and evolved to enhance the activity of the native ligand. Further evolution can be performed to improve variables such as serum half-life, specificity, or immunogenicity.

Evolution of Novel Diagnostic MAbs.

There is a pressing need for improved methods to detect a variety of antigens. One example is the detection of biological warfare (BW) agents.

The antibody phage-display platform herein generates MAbs to many conceivable antigens, such as BW agents, and directed evolution (e.g., recombination and mutagenesis procedures such as nucleic acid shuffling in combination with appropriate selection procedures) optimizes their diagnostic capabilities. There is a considerable amount of interest in this field; as of 1999, DARPA and the DOD have pledged over $30 million to private companies to develop BW detection systems (BioCentury, 7:29), the most promising of which are antibody-based (Hock (1997) "Antibodies for immunosensors: A review" *Analytica Chimica Acta* 347: 177-186). An extension of this work is to optimize clinical diagnostics for established (HIV, hepatitis B, herpes, etc.) and emerging (hepatitis C, viral encephalitis, ebola, etc.) diseases.

Evolution of MAbs for Novel Functions.

Accessing non-human diversity. The references herein describe a variety of recombination (e.g., shuffling) protocols in which families of related sequence are recombined (directly as in DNAse mediated procedures) or indirectly (as in oligonucleotide and in silico shuffling procedures). These protocols are adapted to the present invention by recombining (e.g., shuffling) antibody genes or homologues from related species or alleles.

The repertoire of V genes from common donors (human, mouse, rabbit) can be expanded by recombining (e.g., shuffling) with V gene libraries from a wide range of vertebrate species shown to have an adaptive immune system (Litman et al. (1993) "Phylogenetic diversification of immunoglobulin genes and the antibody repertoire" *Mol Biol Evol* 10: 60-72). Immunoglobulin genes have now been sequenced from several uncommon vertebrates, including camel (Arbabi Ghahroudi et al. (1997) "Selection and identification of single domain antibody fragments from camel heavy-chain antibodies" *FEBS Lett* 414: 521-6), possum (Belov et al. (1999) "Isolation and sequence of a cDNA coding for the heavy chain constant region of IgG from the Australian brushtail possum, Trichosurus vulpecula" *Mol Immunol* 36: 535-41), chicken (Davies et al. (1995) "Selection of specific phage-display antibodies using libraries derived from chicken immunoglobulin genes" *J Immunol Methods* 186: 125-35; Yamanaka et al. (1996) "Chicken monoclonal antibody isolated by a phage display system" *J Immunol* 157: 1156-62), cow (O'Brien et al. (1999) "Generation of native bovine mAbs by phage display" *Proc Natl Acad Sci USA* 96: 640-5), salmon (Hordvik et al. (1999) "Molecular cloning and phylogenetic analysis of the Atlantic salmon immunoglobulin D gene" *Scand J Immunol* 50: 202-10), and many others.

Accessing the diversity of the Ig superfamily. Sequences from other members of the Ig superfamily can be cloned and recombined, or recursively recombined (e.g., shuffled) with existing MAbs to provide additional diversity. A specific example is the use of sequences from the gene family ICAM-1 (CD54) that binds to lymphocyte function-associated antigen 1 (LFA-1, CD11a/CD18), complement receptor 1 (MAC-1, CD11b/CD18), and p150, 95 (CD11c/CD18). More generally, sequences are derived from immunoglobulin homology domains of MHC class II genes or from many cytokine receptors known to share broad homology with Igs. Where sequences are not sufficiently homologous for direct recombination, indirect recombination methods such as oligonucleotide or in silico shuffling can be used.

The T cell receptor genes provide a particularly useful source of diversity. Like the antibody genes themselves, T cell receptors are encoded by a large multigene family which is subject to recombination in the generation of an intact T cell receptor. Also, similarly to antibodies, the T cell receptor has antigen binding as a primary function. To make use of this diversity, two general approaches are used. T cell receptor gene sequences can be provided as substrates for recombination and mutagenesis (e.g., shuffling) reactions as described above. Alternatively, T cell receptor genes are used to create display libraries which are selected for binding to a target of interest. The selected genes can then be recombined with antibody gene segments to produce antibodies with novel binding specificities. In addition, T cell receptor libraries are useful in the selection and optimization of novel, improved T cell receptors which bind to a target of interest.

T-bodies. Antibody genes have been used to replace the T cell receptor in order to allow T cells to be activated by binding to, for example, a cell surface protein via and antigen-antibody interaction rather than an MHC-TCR interaction (Eshhar (1997) "Tumor-specific T-bodies: towards clinical application" *Cancer Immunology and immunotherapy* 45: 131-136). Since MAbs are not naturally optimized for this application, recursive DNA recombination procedures (e.g., nucleic acid shuffling) areparticularly useful for improving upon the reactivity of MAbs when fused to the TCR to improve upon the therapeutic uses of such T-bodies.

Modifying Antibody Effector Function.

The methods of the present invention provide a means of modifying the effector domain as well as the antigen binding domain of antibodies. The heavy chain constant region consisting of the CH2 and CH3 domains, and corresponding to the Fc domain derived by pepsin digestion of an antibody molecule, is the mediator of antibody effector function. The humoral immune response, of which antibody mediated adaptive immunity is one component, involves numerous other factors for the neutralization and elimination of pathogens. On one hand, the complement cascade directly and indirectly mediates the lysis of such pathogens as bacteria. In the classical pathway, the Clq complement component binds directly to the Fc domain of bound IgM or IgG resulting in the activation of a serine protease component. Proteolytic fragments of downstream complement molecules result in opsonization and subsequent phagocytosis and in stimulating a local inflammatory response. In the alternative complement pathway, complement components recognized by specific complement receptors, and bound antibody recognized by Fc receptors synergistically facilitate uptake and destruction of bacterial pathogens by macrophages and other phagocytic cells.

Various Fc receptors are present on non-antigen binding cells of the immune system such as macrophages, neutrophils, natural killer cells, mast cells and eosinophils. Through binding of Fc receptors, the functional attributes of the different cells bearing them are brought into play during an immune response. By increasing or altering the affinity of binding between an antibody and one or more of the various Fc receptors, the efficacy of an antibody can be enhanced. For example, by altering the binding coefficient of an IgG subclass for the Fc receptor, the concentration of antibody required for a therapeutic application can be decreased. In recent clinical trials of the therapeutic antibody, OKT3, prevention and treatment results were disappointing (Woodle et al. (1999) *Transplantation* 15:608). The effectiveness of this molecule was likely limited by the T cell activation properties of its Fc region. Fc variants with decreased Fc-receptor binding activity can rectify these poor results. The recombination and mutagenesis procedures described herein, e.g., DNA shuffling provides a method to produce and isolate such variants.

Fc fusion proteins, i.e., immunoadhesins, are being created and evaluated for a number of disease indications. Fc variants (such as shuffled Fc variants) with altered properties produced by the methods of the invention can be selected to improve these therapeutic reagents. For example, Christen et al. (1999) *Hum Immunol* 60:774, describe results of clinical studies of a TNF receptor-Fc fusion protein in the treatment of rheumatoid arthritis. The patients develop antibodies to the Fc region. The methods of the present invention are useful for generating recombinant (e.g., shuffled) Fc regions with decreased immunogenicity. Antibodies with reduced immunogenicity, e.g., that are humanized or otherwise lack B or T cell epitopes involved in the host immune response, can be selected for use as therapeutic reagents, thereby, avoiding or minimizing the host antibody response. Alternatively, Fc variants can be isolated that elicit a stronger Ab response or modulate the response in other, desirable ways.

In another study, IL-2/Fc fusion proteins were investigated for the treatment of autoimmune disease. The IL-2 moiety is proposed to target recently activated T cells, while the Fc region is thought to result in host T cell killing by both antibody-dependent cell-mediated cytotoxicity and complement-dependent cytotoxicity. The methods of the present invention provide a means to improve both types of Fc mediated killing function of the IL-2 or other Fc fusion proteins, e.g., by increasing Fc receptor binding efficacy, or increasing activation of complement.

In yet another application, Yuan et al. (1999) *Oral Microbiol Immunol* 14:172, propose that an increased concentration of soluble Fc gamma RIII in periodontal lesions may limit phagocytosis and immune homeostasis in this disease. The DNA diversification (e.g., shuffling) techniques of the present invention can be used to generate and select therapeutic antibodies with reduced binding affinity of Fc receptors, providing an alteration in binding kinetics similar to that seen with administration of soluble Fc receptors. Production of antibodies deficient in Fc gamma RIII binding that result in a reduction in phagocytosis offer a potential reagent useful in treatment of periodontal lesions.

To modify the Fc portion of an antibody, CH2/CH3 domains, as either a fragment or in the context of an intact antibody, can be recombined and/or mutated (e.g., shuffled) according to any of the formats discussed herein. For example, recursive sequence recombination procedures such as nucleic acid shuffling can be performed on nucleic acids corresponding to the Fc domain or to the entire antibody molecule. In the former case, an expression cassette designed to accept the CH2/CH3 region into a cloning site can be used to provide and/or express an intact antibody molecule. Screening can be performed by assaying any one of a number of biologically relevant functions, e.g., neutralization, opsonization, phagocytosis, complement mediated lysis, antibody-dependent cell-mediated cytotoxicity, in vivo or by in vitro correlates which can be performed in a high throughput format.

For example, to select for improvements in the ability of an antibody to activate complement, an expression cassette incorporating an antibody antigen binding domain specific for a bacterial pathogen can be used. CH2/CH3 domain nucleic acids can be cloned into the cassette to give rise to antibodies specific for the pathogen with a variety of constant regions and an identical antigen binding specificity. After recombination, by any of the methods previously discussed, the resulting antibodies can be evaluated by a number of in vivo and in vitro methods. Pools of antibodies can be injected into an experimental host, such as a mouse, which is then subjected to a lethal pathogenic challenge. Improved survival rates conferred by the antibodies can readily be assessed. Alternatively, or in combination, in vitro assays measuring lysis of bacterially infected cells in vitro by antibody-dependent cell-mediated cytotoxicity can be performed. High throughput formats for measuring Clq binding and activation of the proteolytic components of complement can also be utilized. Similarly, screening methods can be employed which evaluate Fc receptor binding, serum half-life, phagocytosis, or other functions specific to the antibody or application of interest.

Humanizing Antibodies

Detailed methods for known ways of preparing chimeric (humanized) antibodies can be found e.g., in U.S. Pat. No. 5,482,856, and in a variety of standard texts, including e.g., Borrebaeck (ed) (1995) *Antibody Engineering, 2$^{nd}$ Edition* Freeman and Company, NY (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul).

Humanized antibody molecules of the present invention typically include 1) CDRs of light and heavy chain variable domains from a non-human antibody; and 2) light and/or heavy chain variable domain framework regions derived from and incorporating the sequence diversity of human light and heavy chain variable domain sequences of at least two different human subgroups, groups, families or classes of human light and/or heavy chain molecules, respectively.

Humanized antibodies are especially desirable in applications where the antibodies are used as therapeutics in vivo in human patients. Human antibodies consist of characteristically human immunoglobulin sequences. For example, humanized antibodies can be produced in trioma cells. Genes encoding the antibodies are then cloned and expressed in other cells, such as nonhuman mammalian cells. The general approach for producing human antibodies by trioma technology is described by Ostberg et al. (1983), *Hybridoma* 2: 361-367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

In one useful embodiment, this invention provides for fully humanized antibodies against a target. These can be produced by diversification, e.g., by DNA shuffling or other recombination and/or mutagenesis procedures, of non-human antibody genes followed by humanization by standard humanization methods, e.g., in the references noted herein. In addition to such standard methods for humanization of antibodies, the present invention provides additional mechanisms for humanizing antibodies utilizing DNA diversification (e.g., shuffling) methods.

For example, the conversion of existing antibodies to more humanized forms can be performed directly by recombination methods, such as nucleic acid shuffling. In particular, using recursive sequence recombination procedures (e.g., shuffling), homologous nucleic acids are recombined (as described above, there are many different recombination and/or mutagenesis formats, including various shuffling formats). In the context of the present invention, human libraries of antibody genes (e.g., naïve or targeted libraries as noted above) are recombined with the gene(s) for an antibody of interest and the products of the recombination are selected (as noted in detail in the cited references herein, it is occasionally useful to recombine nucleic acids for more than one cycle prior to selection, and this approach is also appropriate herein). This process is recursively repeated, resulting in new humanized antibodies which comprise amino acid regions corresponding to the starting antibody at positions which confer activity, but which are otherwise humanized. Antibody coding nucleic acids can be sequenced and the information used to design additional recombination partners or to perform in silico recombination.

Briefly, the procedure outlined below can be used to generate a humanized Ig heavy chain variable domain incorporating variant or recombinant, e.g., shuffled, murine CDR amino acid sequences and variant or recombinant Ig heavy chain variable domain framework amino acid sequences. A similar procedure can also be used to prepare a humanized Ig light chain variable domain made up of variant or recombinant murine Ig CDR amino acid sequences and variant or recombinant human Ig light chain variable domain framework amino acid sequences.

First, a murine, or other non-human, antibody of interest (termed the "donor" antibody) is selected. Typically, selection is based on target binding characteristics. The CDR sequences for producing the immunoglobulins of the present invention can be derived from monoclonal antibodies, or, e.g., from antigen specific B cells, capable of binding to the pre-determined antigen, and made by well known methods in any convenient mammalian source including, e.g., mice, hamsters, rats, rabbits, dogs, cats, monkeys, or other vertebrates, capable of producing antibodies. In some cases, the CDR sequences are diversified prior to recombination or assembly as described below. Source cells for the constant region and framework DNA sequences can be obtained from a number of sources, including, e.g., a variety of human cells, including naïve and mature B cells or B cell progenitors, bone marrow derived cells, B cell lines, B cell lymphomas, plasmacytomas, etc.

Typically, the amino acid sequences of at least the first three framework ("FR") regions of the heavy chain variable domain of the donor murine Ig and the first two CDRs of the donor murine Ig are determined.

Starting from the N-terminal, approximately the first 100 amino acids of the N-terminal of the heavy chain variable domain sequence of the donor murine Ig are divided into three FRs and two CDRs as defined by the CDR definitions of both Kabat et al., SEQUENCES OF PROTEINS OF IMMUNOLOGICAL INTEREST, US Dept. Health and Human Services, NIH, USA, (5$^{th}$ ed. 1991) and Chothia and Lesk, *J. Mol. Biol.* (1987) 196:901-917, each of which is incorporated herein by reference in its entirety for all purposes. Using Kabat's numbering system for amino acid residues of an immunoglobulin, the amino acids of the CDRs and framework regions are as follows: CDR1 (amino acids 26-35); CDR2 (amino acids 50-65); FR1 (amino acids 1-25); FR2 (amino acids 36-49); and FR3 (amino acids 66-100). Where the amino acid sequence of the donor murine Ig variable domain is greater than 66 amino acids, amino acid residues in positions greater than position 66 (e.g., amino acid residues 66-100 as in the present example) can be included in framework 3. Optionally sequences corresponding to CDR3 and FR4 are also included.

A library of sequences of framework regions of human Ig heavy chain variable domains is then prepared for diversification, e.g., recombination or recursive recombination, as follows: Using the Kabat numbering system, each murine Ig heavy chain variable domain framework amino acid sequence and murine Ig CDR amino acid sequence is aligned (e.g., by aligning electronically or manually) with all or a portion (subset) of the human heavy chain variable domain framework amino acid sequences and CDR amino acid sequences included in the Kabat database using the SeqhuntII program's Match function or an equivalent alignment program. In some cases, it is desirable to elect a predetermined number of mismatches to insure that the final recombinant heavy chain framework region possesses a desired degree of similarity to the donor heavy chain framework amino acid sequence. For example, if the number of mismatches is chosen to be greater than or equal $0.35\times$ the number of residues in a given framework, then the resulting recombinant heavy chain framework amino acid sequence is less than 65% identical to the donor heavy chain framework amino acid sequence.

Typically, 2 or more (most typically between 2 and 5) human Ig heavy chain variable domain framework amino acid sequences that are relatively divergent from the donor murine Ig heavy chain variable domain framework amino acid sequence (e.g., wherein the amino acid sequence of the Ig heavy chain variable domain framework is less than 65% identical to the amino acid sequence of the donor murine Ig heavy chain variable domain framework). These sequences comprise a set. The selected sequences can include members of a particular family, group, or subgroup of human Ig heavy chain framework amino acid sequences. In some cases, it is preferable to choose only those human sequences in the same subgroup for the set of sequences.

Using the selected set of human Ig heavy chain variable domain framework amino acid sequences, one or more libraries of nucleotide sequences inferred from the framework amino acid sequences are provided. In one preferred embodiment, the sequences are synthesized according to the following protocol: 1) the amino acid sequences of the set of human Ig heavy chain variable domain frameworks are artificially recombined such that the resulting polynucleotide includes elements from multiple component sequences and does not correspond to any single contributing sequence element; 2) if the amino acid residue of the murine sequence at any position differs from an amino acid residue at the same position of any one or more sequence of the set of human sequences, the murine amino acid residue at that position is not included in the synthesized polynucleotide, instead only an amino acid residue derived from a sequence of the set of human Ig heavy chain variable domain framework amino acid sequences is used; 3) the library is prepared by implanting (e.g., by cutting and pasting, hybridizing, ligating synthetic oligonucleotides, etc.) the amino acid sequences for the non-human, e.g., murine, CDR1 and CDR2 into their respective positions (i.e., based on Kabat numbering system) in each synthetically designed heavy chain framework amino acid sequence; 4) a library of degenerate oligonucleotide sequences corresponding to each synthetically recombined, e.g., shuffled, humanized heavy chain variable domain sequence in (3) is then synthesized. It will be appreciated that the same methods apply equally to as few as a single CDR in combination with two framework regions or to all three CDRs in combination with four framework regions. Furthermore, it will be understood that any method for providing fragments corresponding to CDR and framework region sequences can be used as an alternative to the synthetic oligonucleotides described in detail above.

Following a similar procedure, libraries of degenerate oligonucleotide sequences corresponding to humanized Ig light chain variable domains are designed using non-human, e.g., murine, CDRs and a set of human Ig light chain variable domain framework regions. In this instance, based on the Kabat numbering system, the murine CDRs consist of amino acid residues 24-34 (L1), 50-56 (L2), and 89-97 (L3) in human $V_L$, with synthetically recombined framework sequences comprising the remaining portions of the humanized light chain variable domain.

The recombinant, e.g., synthetically shuffled, oligonucleotides in each library are then assemble to produce libraries of intact coding sequences for heavy and light chain variable domains, respectively. If desired, the assembled variable regions are further diversified by any one or more of the diversity generating procedures described or cited herein. These coding sequences are then rescued, e.g., by PCR amplification or digestion with a restriction enzyme and cloned into an appropriate display vector, e.g., a ScFv display vector for expression in a bacterial, yeast or mammalian, e.g., COS, cell. Alternatively, a phage display format can be used. For expression in bacterial or yeast cells, single chain antibodies are typically preferred. In mammalian cells, Fab fragments or intact antibodies are also favorably expressed.

In cases where an intact antibody is preferred, humanized heavy and light chain variable regions are cloned in frame with a human constant region, e.g., naturally occurring human immunoglobulin constant region from a corresponding Ig group or subgroup.

The synthetically recombined antibody sequences are then expressed either constitutively or inducibly, depending on the display vector selected, and the resulting antibodies are screened for binding and/or other properties. For example, the cells displaying the synthetically recombined antibodies are stained with a labeled antigen or ligand, e.g., labeled with FITC, rhodamine, biotin, etc., and sorted by flow cytometry using direct or indirect detection of the labeled ligand.

The antibody encoding genes are then recovered, (e.g., by PCR or other amplification method, or by cloning) from the positively stained cells. Optionally, the labeling and sorting process is repeated using decreasing concentrations of labeled ligand until a desired enrichment for high affinity clones is obtained. Typically 2-3 cycles of labeling and sorting is sufficient to produce a pool of high affinity humanized antibody clones.

At this point, further increases in affinity (i.e., "affinity maturation") can be accomplished using, e.g., any of the diversification procedures described herein. For example, two or more of the "best" (e.g., highest affinity) clones are recombined in vitro or in vivo to produce second round libraries which are in turn screened, e.g, as described above using labeled ligand detected by flow cytometry. Alternatively, the best clones can be sequenced and recombined in silico, or oligonucleotides can be synthesized and recombined as described above. The process of diversification and selection, e.g., by flow cytometry can be performed recursively a desired affinity is obtained.

The humanized antibody genes identified according to this procedure can then be cloned into secretion vectors and transfected into appropriate cell lines for expression of soluble antibodies or fragments. The affinities and/or avidities of the expressed soluble antibodies can then be measured, e.g., by ELISA, biacore, etc. Alternatively, the synthesized and assembled antibody sequences can be cloned into secretion vectors without screening and assayed directly for binding activity.

Optionally, a "benchmark" humanized antibody comprising donor non-human CDRs and the human consensus framework regions (as defined by Kabat et al., supra) is prepared for comparative purposes. For example, the benchmark antibody typically comprises: 1) a heavy chain variable domain of a donor non-human (e.g., murine) CDR1 and CDR2 amino acid sequences (occupying amino acid positions 26-35 and 50-65, respectively, using the Kabat numbering system) and consensus sequences for the human heavy chain variable domain frameworks FR1, FR2, and FR3 (occupying amino acid positions 1-25, 36-49, and 66-100, respectively, using the Kabat numbering system); and 2) a light chain variable domain comprising the donor murine CDR1 and CDR2 amino acid sequences (occupying amino acid positions 24-34 and 50-56, respectively) and consensus sequences for the human heavy chain variable domain frameworks FR1, FR2, and FR3 (occupying amino acid positions 1-23, 35-49, and 56-100 of the naturally occurring murine Ig heavy chain variable domain sequence, respectively. Optionally, the CDR3 and FR4 domains for both heavy and light chains are also included.

The consensus sequences of the human heavy chain and light chain variable frameworks are defined in Kabat et al., SEQUENCES OF PROTEINS OF IMMUNOLOGICAL INTEREST ($5^{th}$ ed. 1991), supra. All human light and heavy chain variable domain amino acid sequences are grouped into "subgroups" of light and heavy chain variable domain amino acid sequences, respectively, that are particularly homologous to each other and have the same amino acids at certain critical positions. The consensus sequence for a particular group or subgroup of related Igs comprises the amino acid which occurs most frequently at a particular amino acid position among the members of the Ig group or subgroup. If two amino acids occurs equally frequently at a particular position for a given Ig group or subgroup, either amino acid can be included in the consensus sequence. Kabat provides a list of the most frequent amino acids at each position in the human variable domain for each subgroup of light and heavy chains. See also Winnaker, *From Genes to Clones* (Verlagsgesellschaft, Weinheim, Germanu, 1987), which is incorporated herein by reference in its entirety for all purposes.

The benchmark humanized antibody can also include corresponding human heavy and light chain constant regions, e.g., if subsequent expression of an intact antibody is desired. Human constant region nucleic acid sequences for use in preparing immunoglobulins of the present invention can be isolated in accordance with well known procedures from a variety of human cells, including naïve and mature B cells or B cell progenitors, bone marrow derived cells, B cell lines, B cell lymphomas, plasmacytomas, etc. (see, e.g., Kabat et al., supra).

The benchmark antibody is used for comparative purposes, e.g., to determine the relative antigen binding affinity or specificity of a humanized antibody of the present invention with respect to the antigen binding affinity or specificity of the benchmark antibody. If desired, the binding affinity of a selected humanized single chain antibody (ScFv antibody) can be compared with the binding affinity of a benchmark single chain antibody. Typically, the affinity of a humanized antibody produced by the methods of the invention is in the range of 4 times, or more, greater that the affinity of the original murine antibody.

The humanized immunoglobulins of the present invention offer a number of significant advantages relative to antibodies derived directly from human or non-human sources. Because the CDRs, i.e., the antigen binding site, are derived from a non-human, e.g., mouse, hamster, sheep, goat, monkey, etc., source, experimental immunization for the production of antibodies, including monocolonal antibodies, is facilitated relative to obtaining high affinity antibodies directly from human sources. Secondly, while the variable domain framework amino acid sequences are derived entirely from sequences of human origin, they do not consist exclusively of the human consensus framework amino acid sequence, providing additional diversity from which to recover humanized antibodies with high antigen binding affinity and specificity. Thirdly, a semi-rational design strategy is employed to produce synthetic heavy and/or light chain framework sequences in which no murine amino acid residue is used at any position in which an amino acid of any of the naturally occurring human light or heavy chain variable domain framework sequences (of the set of human relatively divergent sequences selected) differs from the amino acid of the murine variable domain framework at the same position. This strategy increases "humanization" without compromising functionality. In addition, the sequence of a humanized heavy or light chain variable domain framework amino acid sequence of the invention is typically less than about 65% identical to the donor heavy or light chain variable domain framework amino acid sequence, respectively. Alternatively, in another aspect, the humanized heavy or light chain variable domain framework amino acid sequence is less than about 95%, 90%, 85%, 80%, 75%, or 70% identical to the donor heavy or light chain variable domain framework amino acid sequence.

Humanized antibodies of the present invention have several advantages over non-human, e.g., murine antibodies or chimeric antibodies for use in human therapy. Because the framework of the variable region and the constant region of the humanized immunoglobulin is made up of sequences based on human-derived diversity, the human immune system typically does not recognize these regions as foreign. Consequently, the immune response of a recipient against the humanized antibody is frequently significantly less than the response against an antibody derived exclusively from a non-human organism, or a chimeric antibody containing foreign (non-human), e.g., variable region framework, components. Additionally, humanized antibodies, in particular those antibodies possessing human constant region domains, function more similarly to naturally occurring human antibodies, e.g., with respect to complement fixation, effector function, and the like. Effective treatment procedures for humanized antibodies more closely parallel those used for naturally occurring human antibodies than those procedures typically employed with murine, or other non-human, or chimeric antibodies which typically require higher and more frequent doses due to shorter half life of the murine or chimeric antibody in human circulation.

Coevolution of Antibodies and their Cognate Antigens

An aspect of the present invention relates to the coevolution of an antibody and its cognate antigen. Efforts at developing therapeutic antibody reagents are often hampered by poor antigenicity of the target antigen. This poor antigenicity is sometimes the result of the high degree of similarity between the target antigen and self antigens of the organism being immunized. In such a case, antibodies which react with the target and the self antigen are deleted from the antibody repertoire or are rendered anergic and are unavailable for recovery. Another reason for poor antigenicity is that the target may be an epitope which is available only transiently, for example, an epitope which results from a conformational change induced by binding of the antigen to a receptor. Another factor affecting antigenicity is the accessibility, or lack thereof, of the target epitope. Many antigens of clinical relevance are available only in minute amounts in their native state, and are difficult to isolate and purify. While expression of recombinant proteins often provides a solution, many recombinant proteins form insoluble aggregates in which the relevant antigenic epitopes are inaccessible.

Diversification procedures (such as DNA shuffling) are used in the present invention to address these and other problems to improve antigenicity of target antigens, thereby increasing the repertoire of the antibody response available as a substrate for directed evolution (e.g., shuffling) of antibodies. The application of DNA diversification and selection procedures (such as shuffling) for the coordinated improvement of an antibody and its cognate antigen is referred to herein as "coevolution." Briefly, to apply antibody/antigen coevolution, a candidate antigen is selected from among any of the potential targets described above, e.g., tumor antigens, bacterial antigens, viral antigens. The DNA encoding the target antigen is then subjected to one or more rounds of recombination and/or mutagenesis according to any of the methods (e.g., shuffling) described herein. Libraries of recombinant antigen sequences are screened, and sequences encoding antigens or antigenic peptides with desired properties are selected. Desired properties include stability, solubility, and conformation among others. After an initial screen to select library members with desirable properties, antibodies which bind a selected antigen or selected pool of (e.g., shuffled) library members are raised or selected using the methods described above. The DNA sequences encoding these antibodies then provide the substrates for one or more rounds of diversification and selection, for example by DNA shuffling.

Methods of screening the recombinant antigen library are critical for the success of the coevolution process. Numerous methods are available, and are exemplified in the procedures outlined below. However, it will be apparent to one of skill in the art, that modifications or substitutions of alternative methods will also be applicable. The libraries of recombinant antigen sequences are typically large pools of DNA sequences, while a typical antigen suitable for immunization is an isolated or purified protein. Nonetheless, a number of approaches suitable for screening large libraries are available. For example, naked or conjugated DNA has been used to raise antibodies in a number of organisms, and has been effective as a vaccine in many cases. Pools of library sequences can be used to immunize a model animal, most frequently a mouse, and the resulting antibodies assayed for their ability to bind an informative target, e.g., tumor cells, bacteria, virally infected cells. Optionally, display libraries can be derived from the immunized animal for further evaluation and manipulation. Alternatively, the library DNA can be transcribed and translated in vitro, and the resulting polypeptides used as an immunogen. Another approach is to transform the library sequences and express them in cells. Depending on the vector selected whole cells or cell components can then be used as immunogens. In the case where an existing, albeit sub-optimal, antibody to the target exists, the existing antibody can be used to pre-select cells expressing evolved antigens prior to immunization.

Production of Broadly Neutralizing HIV Antibodies.

Tremendous effort has been expended in the last decade towards developing antigens which induce broadly neutralizing antibodies against HIV. Such an antigen is desirable in the development of vaccines against HIV. The most promising strategies to date have focused on the HIV envelope proteins gp120 and gp41. However, a number of difficulties have continued to plague efforts to produce broadly neutralizing antibodies to these envelope proteins. HIV rapidly mutates and recombines mutant sequences. Broadly neutralizing antibodies must therefore target highly conserved epitopes, of which there are few in HIV. The envelope is highly glycosylated and this is believed to "cloak" conserved epitopes from the humoral immune system. In vivo gp120 and gp41 form a trimeric complex on the surface of the envelope, and it is difficult to mimic this conformation in an antigen formulation. Additionally, this trimeric complex undergoes a conformational change after binding CD4 and CCR5, transiently exposing novel epitopes prior to fusion of the virion with the target cell. These conformational epitopes may be inaccessible to the humoral immune system by virtue of their transient exposure during the fusion process. Furthermore, the gp41 protein is difficult to express and purify despite repeated attempts. Recombinant gp41 froms intractable precipitates when the whole protein or the N-terminal 51 residues are expressed.

The DNA diversification procedures (such as shuffling) described herein provide a means for evolving gp120 and gp41 homologues that can be tractably expressed either as protein or as DNA. Homologues of gp120 and gp41 which are stably expressed in conformations that elicit broadly neutralizing antibodies are selected using one or more prescreens. Candidates which are identified through the prescreening process are then used to immunize mice. The resulting antibodies are then themselves the subject of the diversification procedures, e.g., DNA shuffling of the invention. The following examples describe variations, and are for purposes of illustration rather than limitation, modifications and combinations will be readily apparent to one of skill in the art, and are included within the scope of the present invention.

In Vitro Evolution of a gp120 Envelope Cocktail Vaccine

A vector which utilizes a strong promoter derived from cytomegalovirus and the rev gene of HIV-1 is utilized to provide efficient transcription and stabilization of messenger RNA. Cloning sites are used to introduce gp120 sequences into the vector between the CMV promoter (5') and gp41 encoding sequences (3'). Sequences derived from one or more isolates of HIV corresponding to the respective gp120 genes are cloned into the vector and diversified (e.g., shuffled) in vitro as described herein. The resulting library is screened as follows. Recombined and/or mutated (e.g., shuffled) sequences resulting in translation of an intact gp120 without termination or frameshift leads to synthesis of gp41 protein from the adjacent sequences. When expressed in CD4 positive human cells along with gp120, gp41 has fusogenic activity. To screen the diversified (e.g., shuffled) gp120 library, human 293 cells expressing CD4 are transfected with library plasmids. After incubation under appropriate conditions (37° C., 5% CO2) for 24 hours, fusion of the transfected cells is evaluated microscopically. Library clones which give rise to intact protein are then pooled for immunization. Complex library mixtures, typically comprising 5000-15000 members per 100 µg immunization dose, are then used to immunize a group of mice for subsequent evaluation.

Conformational Epitopes of gp41.

Two conformational states of gp41 are of interest in the induction of broadly neutralizing antibodies against HIV (Biochemistry (1995) 34:14961). The first of these is the so called "resting state" of gp41. Portions of gp41, such as the so-called N-terminal domain which forms a three stranded coiled coil, are highly conserved between HIV subtypes and feature of these sequences are conserved across all retroviruses (i.e. the three stranded coiled coil structure). Peptides derived form the C-terminal helix and stabilized analogs of this helix have been shown to have broadly neutralizing activity against many subtypes of HIV (Judice et al., *Proc. Nat'l. Acad. Sci.* (1997) *USA* 94:1342). The current model suggests that the peptides can bind to the conserved groove on the N-terminal helix trimer and thus inhibit the conformational change involved in fusion to a CD4 cell. Thus antibodies that can gain access to this conserved coiled coil structure either in the resting state or at some point during the fusion event can effectively block fusion.

A second alternative is the "fusogenic" state formed by the three C-terminal helices packed against the coiled coil formed by the N-terminal helices. Biochemical studies on HIV fusion suggest that it takes about 20 minutes from the time the first envelope trimers undergo a conformational change and initiate the fusion process to the point that the HIV virion fuses with the target cell. During this period conformational epitoes corresponding to the fusogenic form of gp41 are exposed to antibodies.

The present invention provides for the recombination (e.g., shuffling) of gp41 gene fragments to generate recombinant gp41 homologues which encode polypeptides which correspond to the "resting state" and "fusogenic" conformational epitopes. Accordingly, DNA fragments corresponding to gp41 homologues can be recombined using any of the methods described in this application. Screening for the conformational epitopes is then perfomed, for example, by assessing the ability of recombinant epitopes to bind peptides or antibodies of interest.

The methods outlined above provide suitable antigen for the production of antibodies, and the sequences encoding them, to serve as substrates for the diversification (e.g., shuffling) methods of the invention. Optimized antibodies against HIV epitopes have great utility in the diagnosis, prevention, and treatment of HIV infection.

In addition, the DNA sequences encoding recombinant (e.g., shuffled) antigen, or portions thereof comprising antigenic peptides and epitopes produced by the methods of the invention can also serve as DNA vaccines. Furthermore, individual recombinant antigens can be expressed to provide material for protein vaccines. Likewise, pools of recombinant antigens can be combined to produce cocktails of recombinant antigens for vaccines. Such vaccines have utility in the generation of HIV neutralizing antibodies in humans.

Further Manipulating Antibody Nucleic Acids

One aspect of the present invention includes the cloning and expression of antibody coding nucleic acids. In addition to the many texts noted above, general texts which describe molecular biological techniques useful herein, including the use of vectors, promoters and many other topics relevant to expressing nucleic acids such as antibodies, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). Examples of techniques sufficient to direct persons of skill through in vitro amplification methods, useful in identifying, isolating and cloning antibody coding nucleic acids, including the polymerase chain reaction (PCR) the ligase chain reaction (LCR), Qᴲ-replicase amplification and other RNA polymerase mediated techniques (e.g., NASBA), are found in Berger, Sambrook, and Ausubel, as well as Mullis et al., (1987) U.S. Pat. No. 4,683,202; PCR *Protocols A Guide to Methods and Applications* (Innis et al. eds) Academic Press Inc. San Diego, Calif. (1990) (Innis); Amheim & Levinson (Oct. 1, 1990) C&EN 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

The present invention also relates to host cells which are transduced with vectors of the invention, and the production of antibody polypeptides of the invention by recombinant techniques. Host cells are genetically engineered (i.e., transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the antibody gene(s) of interest. The culture conditions, such as temperature, pH and the like, are those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein.

The antibodies of the invention can also be produced in non-animal cells such as plants, yeast, fungi, bacteria and the like. Indeed, as noted throughout, phage display is an especially relevant technique for producing antibodies. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Integrated Systems

The present invention provides computers, computer readable media and integrated systems comprising character strings corresponding to diversified (e.g., shuffled) antibodies and antibody-encoding nucleic acids. These sequences can be manipulated by in silico shuffling methods, or by standard sequence alignment or word processing software.

For example, different types of similarity and considerations of various stringency and character string length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package with GOs for calculating sequence similarity is BLAST, which can be adapted to the present invention by inputting character strings corresponding to the sequences herein.

BLAST is described in Altschul et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci.* USA 89:10915).

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

The sequence recombined (e.g., shuffled) antibodies of the invention, or coding nucleic acids, are aligned to provide structure-function information. For example, the alignment of recombinant (e.g., shuffled) antibody sequences which are selected against the same target provides an indication of which residues are relevant for binding to the antigen (i.e., conserved residues are likely more important for activity than non-conserved residues).

Standard desktop applications such as word processing software (e.g., Microsoft Word™ or Corel WordPerfect™) and database software (e.g., spreadsheet software such as Microsoft Excel™, Corel Quattro PrO™, or database programs such as Microsoft Access™ or Paradox™) can be adapted to the present invention by inputting character strings corresponding to variant (e.g., shuffled) antibodies (or coding nucleic acids), e.g., produced (for example, by nucleic acid shuffling) by the methods described herein. For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST or PILEUP can also be incorporated into the systems of the invention for alignment of nucleic acids or proteins (or corresponding character strings).

Integrated systems for analysis in the present invention typically include a digital computer with software for aligning or manipulating sequences, as well as data sets entered into the software system comprising any of the sequences herein. The computer can be, e.g., a PC (Intel x86 or Pentium chip-compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visual basic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operation.

In one aspect, the computer system is used to perform "in silico" sequence recombination or shuffling of character strings. A variety of such methods are set forth in "METHODS FOR MAKING CHARACTER STRINGS, POLYNUCLEOTIDES & POLYPEPTIDES HAVING DESIRED CHARACTERISTICS" by Selifonov and Stemmer, filed Feb. 5, 1999 (U.S. Ser. No. 60/118,854) and "METHODS FOR MAKING CHARACTER STRINGS, POLYNUCLEOTIDES & POLYPEPTIDES HAVING DESIRED CHARACTERISTICS" by Selifonov and Stemmer, filed Oct. 12, 1999 (U.S. Ser. No. 09/416,375). In brief, genetic operators are used in genetic algorithms to change given sequences, e.g., by mimicking genetic events such as mutation, recombination, death and the like. Multi-dimensional analysis to optimize sequences can be also be performed in the computer system, e.g., as described in the '375 application.

A digital system can also instruct an oligonucleotide synthesizer to synthesize oligonucleotides, e.g., used for gene reconstruction or recombination, or to order oligonucleotides from commercial sources (e.g., by printing appropriate order forms or by linking to an order form on the internet).

The digital system can also include output elements for controlling nucleic acid synthesis (e.g., based upon a sequence or an alignment of a recombinant, e.g., shuffled, antibody as herein), i.e., an integrated system of the invention optionally includes an oligonucleotide synthesizer or an oligonucleotide synthesis controller. The system can include other operations which occur downstream from an alignment or other operation performed using a character string corresponding to a sequence herein, e.g., as noted above with reference to assays.

In Vitro Assays and Kits

The present invention provides commercially valuable assays and kits to practice the assays. In the assays of the invention, one or more antibody of the invention is employed to, e.g., detect a target antigen, identify a cell, neutralize an antigen, etc. Such assays are based on any known method in the art, e.g, ELISA, flow cytometry, fluorescent microscopy, plasmon resonance, and the like, to detect binding of an antibody to a target antigen.

Kits based on the assay are also provided. The kits typically include a container, and one or more antibody. The kits optionally comprise directions for performing the assays, additional detection reagents, buffers, or instructions for the use of any of these components, or the like. Alternatively, kits can include cells, vectors, (e.g., expression vectors, secretion vectors comprising an antibody of the invention), for e.g., the expression of an antibody of the invention.

In a further aspect, the present invention provides for the use of any composition, antibody, cell, cell culture, apparatus, apparatus component or kit herein, for the practice of any method or assay herein, and/or for the use of any apparatus or kit to practice any assay or method herein and/or for the use of cells, cell cultures, compositions or other features herein as a therapeutic formulation. The manufacture of all components herein as therapeutic formulations for the treatments described herein is also provided.

EXAMPLES

Example 1

Affinity Maturation of a Human Antibody

Starting materials for artificial affinity maturation by DNA diversification and selection procedures can be derived from any of a variety of human and/or non-human donor sequences. In many cases, it is most convenient to utilize sequences corresponding to monoclonal antibodies derived from hybridomas. However, nucleic acid sequences derived from antigen specific, or even unselected or naïve B cells from immunized human or non-human donors can also be utilized.

For example, to produce a high affinity human antibody specific for a selected target antigen, one or more human derived antibody gene(s) are selected from, e.g., xenomouse hybridomas or naïve human antibody display libraries (e.g., phage display antibodies or other cell surface display formats including bacterial or yeast display formats) to provide the starting materials for artificial affinity maturation, e.g., by DNA recombination or recursive recombination, e.g., shuffling. Alternatively, or in addition, sequences from humanized antibodies can be used.

While sequences originating from naïve B cells, or libraries of sequences can be utilized, especially in cases where sequences from antigen specific cells are unavailable, it is often more desirable to use sequences derived from a target antigen specific cell, such as a B cell or hybridoma. Any target antigen, including protein antigens, carbohydrate antigens, cell fragments or fractions, viral particles, tumor antigen, etc., to which an antibody response can be produced using an appropriate immunization protocol is suitable for producing a target antigen specific antibody response. Similarly, B cells, hybridomas, and other antibody producing cells that are specific for a particular target antigen, e.g., as described above, can provide the starting sequences for affinity maturation by DNA recombination and mutagenesis procedures as described herein. Numerous protocols for eliciting a target antigen specific antibody response are known to those of skill in the art.

Human variable domain sequences that are similar or homologous (or substantially similar or homologous) to the variable domain sequences of the selected antibody gene(s) are identified, e.g., by hybridization, in silico sequence analysis, or other means. Typically, other variable domain sequences from the same or a related human V gene family, group, or subgroup are identified. The identified variable domain nucleotide sequences are then aligned with the corresponding variable domain sequences of the previously selected antibody gene(s). Degenerate oligonucleotides which capture the nucleotide sequence diversity of the identified sequences of the human V gene family, group, or subgroup are designed and assembled to generate libraries of synthetic (recombinant) sequences.

Most commonly, these sequences are then cloned into a cell surface display format (i.e., bacterial, yeast, or mammalian (COS) cell surface display; phage display) for expression and screening. A single chain format is typically preferred for bacterial and yeast display systems, while a Fab or whole antibody format can be favorably expressed in mammalian cells.

The recombinant sequences are transfected (transduced or transformed) into the appropriate host cell where they are expressed and displayed on the cell surface. For example, the cells can be stained with a labeled, e.g., fluorescently labeled, target ligand (i.e., antigen). The stained cells are sorted by flow cytometry, and the antibody encoding genes are recovered, e.g., by PCR or expansion and cloning, from the positive cells. The process of staining and sorting can be repeated multiple times, e.g., using progressively decreasing concentrations of the target ligand until a desired level of enrichment is obtained. Alternatively, any screening or detection method known in the art that can be used to identify cells that bind the target antigen can be employed.

The antibody encoding genes recovered from the target antigen binding cells are then recombined according to any of the methods described herein or in the cited references. The recombinant sequences produced in this round of diversification are then screened by the same or a different method to identify recombinant genes with improved affinity for the target antigen. The diversification and selection process is optionally repeated until a desired affinity is obtained.

The recombinant antibody genes produced by recursive recombination of progressively higher affinity antibody genes are then cloned into an appropriate secretion vector and transfected into a host cell for expression and production of the encoded antibody. The affinity of the soluble antibody can be measured using known techniques, e.g., ELISA, biacore. If the desired affinity has not been achieved, further cycles of recombination and screening can be performed, optionally incorporating diversity from additional sequence elements or mutagenesis procedures.

Example 2

Humanization of a Mouse Monoclonal Antibody

The methods of the present invention can be used to humanize mouse monoclonal antibodies. The following example illustrates selection of starting sequences based on a sequence alignment between a mouse monoclonal antibody with a desired specificity, and a group of related human variable region sequences. The specificity of the antibody selected, and the nucleic acid sequences encoding the selected antibody are not material to the present invention. Indeed, sequences encoding any monoclonal antibody, or even an antibody derived from a polyclonal serum for which the nucleic acid or protein sequence is known or can be determined, e.g., by clonal expansion and sequencing of an antigen specific B cell. Accordingly, the following example is provided as illustration and should not be interpreted to define the scope of the invention.

For example, the amino acid sequence corresponding to a mouse monoclonal antibody specific for tumor necrosis factor (TNF) alpha (SEQ ID NO:1, labeled below as "1"), is aligned with a set of related human antibody sequences, e.g., amino acid sequences inferred from human antibody encoding nucleic acid sequences of the same class and/or family (SEQ ID NO:2, labeled below as "2", Dersimonian et al. (1987) 139:2496-2501; SEQ ID NO:3, labeled below as "3", Griffiths et al. (1993) 12:725-734; SEQ ID NO:4, labeled below as "4", Huang et al. (1992) 89:1331-1343; SEQ ID NO:5, labeled below as "5", Kasaian et el. (1994) 152:3137-3151; and SEQ ID NO:6, labeled below as "6", Welschof et al., (1995) 179:203-214) as follows:

```
        1
*1      EVKLEESGGG LVQPGGSMKL SCVASGFIFS NHWMNWVRQS PEKGLEWVAE

2      Q.Q.VQ..AE VKK..A.V.V ..K...YT.T SYA.H....A .GQR...MGW

3      Q.Q.VQ..AE VKK..A.V.V ..K...YT.T GYY.H....A .GQ....MGW
```

```
 4     Q.Q.VQ..SE  .KK..A.V.V  .RK...YT.T  GYY.N....A  .GQ....MGW

5     Q...VQ..AE  VKK..V.V.V  ..K...STVT  .YAIH....A  .GQR...MGW

6     Q.Q.Q...AE  VRK..A.V.V  ..K...YILT  TYY.H....A  .GQ....MGL

51
*1     IRSKSINSAT  HYAESVKGRF  TISRDDSKSA  VYLQMIDLRI  EDTGVYYCSR

2     .NP..NSGN.  K.SQKFQ..V  ..T..T.A.T  A.MELSS..S  ...A....A.

3     .NP..NSGG.  N..QKFQ..V  ..T..T.A.T  A.MELSS..S  ...A....A.

4     .NT..NTGNP  T..QGFT...  VF.L.T.V.T  A...ISS.KA  ...A....A.

5     .NA..G.GN.  K.SQKFQ..V  ..T..T.ANT  A.MELSS..S  ...A....A.

6     .NP..SGGSG  GNIHKFQ..L  .MT..T.T.T  ..ME.SS..S  ...A..F.A.
```

Framework region (FR) 1 corresponds to amino acid positions 1-25; FR 2 corresponds to amino acid positions 36-49; and FR 3 corresponds to amino acid positions 66-100. Complementarity determining region (CDR) 1 corresponds to amino acid positions 26-35; and CDR 2 corresponds to amino acid positions 50-65. Dots indicate positions of amino acid identity between mouse and human sequences.

Amino acid sequences that are substantially dissimilar from the mouse sequence to be humanized are typically selected. In general, sequences that are less than 65% identical in any of the framework regions are utilized. A comparison of the 5 human sequences listed above to the sequence of the mouse monoclonal antibody yields the following measures of identity:

| 1. | FR1 = 48% | FR2 = 57% | FR3 = 56% |
| 2. | FR1 = 48% | FR2 = 64% | FR3 = 56% |
| 3. | FR1 = 48% | FR2 = 64% | FR3 = 56% |
| 4. | FR1 = 52% | FR2 = 57% | FR3 = 53% |
| 5. | FR1 = 52% | FR2 = 64% | FR3 = 56% |

Oligonucleotides are synthesized that encode the amino acid diversity present in the aligned antibody sequences. At positions within the framework regions that differ between the mouse and any human sequence, the mouse residue is never used. Oligonucleotides encoding the mouse monoclonal antibody CDRs are then incorporated into libraries of synthetic oligonucleotides. Optionally, the CDR3 and/or FR4 regions are similarly aligned and corresponding oligonucleotides synthesized and assembled. In this manner, a library of full-length recombinant variable region sequences is assembled starting only with a set of sequence files corresponding to the non-human antibody to be humanized and two or more (distantly) related human antibody sequences.

Following assembly of the synthesized oligonucleotides into a library of full-length variable regions representing the sequence diversity present in the mouse and human sequence files, the variable region nucleic acids can be recombined and/or mutated, and selected according to any of the methods described herein.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for producing a variant Fc region polypeptide having a desired modified effector function, the method comprising:
   (a) producing a library of variant Fc molecules from Fc nucleic acids each encoding a CH2 domain and/or a CH3 domain, the domains encoded in the context of an intact antibody or a fragment thereof,
   wherein the variant Fc molecules are generated by:
      (i) hybridizing nucleic acids encoding a first CH2 domain and nucleic acids encoding a second CH2 domain and/or hybridizing nucleic acids encoding a first CH3 domain and nucleic acids encoding a second CH3 domain from the Fc nucleic acids, and
      (ii) extending the resulting hybridized nucleic acids using a polymerase;
   (b) expressing the library to produce variant Fc region polypeptides;
   (c) screening the library of variant Fc region polypeptides to identify an expressed variant Fc region polypeptide having a modified effector function; and
   (d) repeating steps (a) through (c) one or more times until the expressed variant Fc region polypeptide has acquired the desired modified effector function.

2. The method of claim 1, comprising screening the variant Fc region polypeptides in vitro.

3. The method of claim 2, wherein the screening is performed by an assay selected from the group consisting of Fc receptor binding, complement fixation, complement mediated cell lysis, and activation of a proteolytic complement component, and flow cytometry.

4. The method of claim 1, comprising screening the variant Fc region polypeptides in vivo.

5. The method of claim 4, wherein the screening is performed by an assay selected from the group consisting of serum half-life, pathogenic challenge, toxin neutralization, small molecule clearance, half-life extension of a protein pharmaceutical, and tumorigenesis.

6. The method of claim 1, wherein the modified effector function is selected from the group consisting of Kd of Fc receptor binding, Kd of C1q binding, and activation of C1q proteolytic activity.

7. The method of claim 1, wherein step (a) is repeated one or more times.

8. The method of claim 1, wherein the library of diverse recombinant immunoglobulin constant region nucleic acids is produced by one or more rounds of recursive recombination.

9. The method of claim 1, wherein step (a) comprises sexual PCR mutagenesis.

10. The method of claim 1, wherein step (a) comprises synthetic recombination.

11. The method of claim 1, wherein nucleic acids encoding a first CH2 domain and a second CH2 domain and/or a first CH3 domain and a second CH3 domain are generated by fragmentation of the Fc nucleic acids.

12. The method of claim 1, wherein nucleic acids encoding a first CH2 domain and a second CH2 domain and/or a first CH3 domain and a second CH3 domain are overlapping CH2 domain and/or CH3 domain oligonucleotides.

* * * * *